US010470719B2

(12) United States Patent
Shimol et al.

(10) Patent No.: US 10,470,719 B2
(45) Date of Patent: Nov. 12, 2019

(54) MACHINE LEARNT MODEL TO DETECT REM SLEEP PERIODS USING A SPECTRAL ANALYSIS OF HEART RATE AND MOTION

(71) Applicant: Verily Life Sciences LLC, Mountain View, CA (US)

(72) Inventors: David Ben Shimol, San Francisco, CA (US); Ali Shoeb, Mill Valley, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 231 days.

(21) Appl. No.: 15/421,349

(22) Filed: Jan. 31, 2017

(65) Prior Publication Data

US 2017/0215808 A1 Aug. 3, 2017

Related U.S. Application Data

(60) Provisional application No. 62/289,796, filed on Feb. 1, 2016.

(51) Int. Cl.
*A61B 5/00* (2006.01)
*A61B 5/0205* (2006.01)
(Continued)

(52) U.S. Cl.
CPC .......... *A61B 5/7267* (2013.01); *A61B 5/0002* (2013.01); *A61B 5/0205* (2013.01);
(Continued)

(58) Field of Classification Search
USPC ........................................................ 702/181
See application file for complete search history.

(56) References Cited

U.S. PATENT DOCUMENTS 8,758,242 B2 * 6/2014 Miesel ................. A61B 5/0476
600/301
2013/0289424 A1 10/2013 Brockway et al.
(Continued)

FOREIGN PATENT DOCUMENTS

WO 2017040331 A1 3/2017

OTHER PUBLICATIONS

Popovic et al., "Automatic scoring of sleep stages and cortical arousals using two electrodes on the forehead: validation in healthy adults," J. Sleep Res. 23(2), pp. 211-221 (Apr. 2014).
(Continued)

*Primary Examiner* — Paul D Lee
(74) *Attorney, Agent, or Firm* — Perkins Coie LLP

(57) ABSTRACT

The present disclosure relates to systems and methods for probabilistically estimating an individual's sleep stage based on spectral analyses of pulse rate and motion data. In one implementation, the method may include receiving signals from sensors worn by the individual, the signals including a photoplethysmographic (PPG) signal and an accelerometer signal; dividing the PPG signal into segments; determining a beat interval associated with each segment; resampling the set of beat intervals to generate an interval signal; and generating signal features based on the interval signal and the accelerometer signal, including a spectrogram of the interval signal. The method may further include determining a sleep stage for the individual by comparing the signal features to a sleep stage classifier included in a learning library. The sleep stage classifier may include one or more functions defining a likelihood that the individual is in the sleep stage based on the signal features.

26 Claims, 9 Drawing Sheets

(51) Int. Cl.
*A61B 5/024* (2006.01)
*G16H 50/20* (2018.01)
*A61B 5/11* (2006.01)

(52) U.S. Cl.
CPC ........ *A61B 5/02416* (2013.01); *A61B 5/4809* (2013.01); *A61B 5/4812* (2013.01); *A61B 5/7246* (2013.01); *A61B 5/7275* (2013.01); *G16H 50/20* (2018.01); *A61B 5/02405* (2013.01); *A61B 5/11* (2013.01); *A61B 2562/0219* (2013.01)

(56) References Cited

U.S. PATENT DOCUMENTS

| | | | |
|---|---|---|---|
| 2014/0275854 A1 | 9/2014 | Venkatraman et al. | |
| 2016/0192716 A1* | 7/2016 | Lee ........................ | G06F 3/015 2/422 |
| 2016/0192857 A1* | 7/2016 | Lee ........................ | A61B 5/681 600/382 |
| 2017/0055898 A1* | 3/2017 | Bandyopadhyay .. | A61B 5/4812 |
| 2017/0347948 A1* | 12/2017 | Thein ................. | A61B 5/02405 |
| 2017/0360361 A1* | 12/2017 | Long .................. | A61B 5/02438 |
| 2017/0360363 A1* | 12/2017 | Fonseca ............... | A61B 5/7264 |
| 2018/0000408 A1* | 1/2018 | Heinrich ............... | A61B 5/0452 |
| 2018/0042540 A1* | 2/2018 | Kinnunen ............... | A61B 5/16 |
| 2018/0085000 A1* | 3/2018 | Weffers-Albu ...... | A61B 5/7246 |
| 2018/0125418 A1* | 5/2018 | Haakma ............... | A61B 5/0205 |

OTHER PUBLICATIONS

Levendowski et al., "Retrospective cross-validation of automated sleep staging using electroocular recording in patients with and without sleep disordered breathing," International Archives of Medicine 5:21, 9 pages (Jun. 2012).

Stepnowsky et al., "Scoring accuracy of automated sleep staging from a bipolar electroocular recording compared to manual scoring by multiple raters," Sleep Medicine 14, pp. 1199-1207 (Aug. 2013).

International Searching Authority, "International Search Report and Written Opinion", for related PCT Patent Application No. PCT/US2017/015860, dated May 4, 2017, 13 pages.

* cited by examiner

MACHINE LEARNT MODEL TO DETECT REM SLEEP PERIODS USING A SPECTRAL ANALYSIS OF HEART RATE AND MOTION

CROSS-REFERENCE TO RELATED APPLICATION(S)

This application claims the benefit of priority of U.S. Provisional Application No. 62/289,796, filed Feb. 1, 2016, which is expressly incorporated herein by reference in its entirety. In addition, systems and methods of the present application may include one or more processes disclosed in U.S. Provisional Application No. 62/289,781, filed Feb. 1, 2016, which is expressly incorporated herein by reference in its entirety.

TECHNICAL FIELD

The present disclosure generally relates to computer-implemented systems and methods for measuring physiological parameters of an individual. More particularly, and without limitation, the disclosed embodiments relate to systems and methods for detecting an individual's sleep stage using spectral analyses of pulse rate and motion data.

BACKGROUND

Determining an individual's sleep patterns can provide useful health information, such as information relating to an individual's sleep habits, sleep quality, sleep duration, and other physiological parameters. Many individuals may wish to determine their sleep stage, for example, to assess their general health level, detect sleeping abnormalities or disorders, and identify personal sleeping patterns. In addition, such information may be useful for detecting precursors to physiological conditions such as Parkinson's disease, PTSD, Major Depression, Alzheimer's Disease, and other such measures.

Conventional methods for determining an individual's sleep stage suffer from numerous drawbacks and can fail to provide accurate results. When using conventional measurement systems and techniques, several factors can impair sleep stage determinations.

SUMMARY

The disclosed embodiments may include computer-implemented systems and methods for detecting an individual's sleep stage by using spectral analysis of pulse rate and motion data. The disclosed embodiments may include, for example, a computer-implemented method for probabilistically estimating an individual's sleep stage. The method may be implemented using one or more processors and may include receiving a set of signals from a set of sensors worn by the individual. The set of signals may include a photoplethysmographic (PPG) signal and/or an accelerometer signal. The method may further include determining whether the received PPG signal comprises segments having equal time durations and dividing the PPG signal into a set of equally-timed segments if the received PPG signal comprises segments having unequal time durations. The method may also include determining a beat interval associated with each segment. The beat interval may reflect an elapsed time between successive heartbeats of the individual. The method may also include sampling the set of beat intervals to generate an interval signal. The beat intervals may be sampled using the same frequency as that of the equally-timed segments of the PPG signal or may be sampled using a different frequency than that of the equally-time segments of the PPG signal. The method may also include generating a set of signal features based on the interval signal and the accelerometer signal. The set of signal features may include a spectrogram of the interval signal. The method may also include determining a sleep stage for the individual by operating on the set of signal features using a sleep stage classifier included in a learning library. The sleep stage classifier may include a set of functions defining a likelihood that the individual is in the sleep stage based on the set of signal features.

The disclosed embodiments may also include, for example, a computer-implemented system for probabilistically estimating an individual's sleep stage. The system may include a memory storing instructions and one or more processors configured to execute the instructions to perform one or more operations. The operations may include receiving a set of signals from a set of sensors worn by the individual. The set of signals may include a photoplethysmographic (PPG) signal and/or an accelerometer signal. The operations may further include determining whether the received PPG signal comprises segments having equal time durations and dividing the PPG signal into a set of equally-timed segments if the received PPG signal comprises segments having unequal time durations. The operations may also include determining a beat interval associated with each segment. The beat interval may reflect an elapsed time between successive heartbeats of the individual. The operations may also include sampling the set of beat intervals to generate an interval signal. The beat intervals may be sampled using the same frequency as that of the equally-timed segments of the PPG signal or may be sampled using a different frequency than that of the equally-time segments of the PPG signal. The operations may also include generating a set of signal features based on the interval signal and the accelerometer signal. The set of signal features may include a spectrogram of the interval signal. The operations may also include determining a sleep stage for the individual by operating on the set of signal features using a sleep stage classifier included in a learning library. The sleep stage classifier may include a set of functions defining a likelihood that the individual is in the sleep stage based on the set of signal features.

The disclosed embodiments may also include, for example, a tangible, non-transitory computer-readable medium storing instructions, that, when executed by at least one processor, cause the at least one processor to perform a method for probabilistically determining an individual's sleep stage. The method may include receiving a set of signals from a set of sensors worn by the individual. The set of signals may include a photoplethysmographic (PPG) signal and/or an accelerometer signal. The method may further include determining whether the received PPG signal comprises segments having equal time durations and dividing the PPG signal into a set of equally-timed segments if the received PPG signal comprises segments having unequal time durations. The method may also include determining a beat interval associated with each segment. The beat interval may reflect an elapsed time between successive heartbeats of the individual. The method may also include sampling the set of beat intervals to generate an interval signal. The beat intervals may be sampled using the same frequency as that of the equally-timed segments of the PPG signal or may be sampled using a different frequency than that of the equally-time segments of the PPG signal. The method may also include generating a set of signal features based on the interval signal and the accelerometer signal. The set of signal features may include a spectrogram of the interval signal. The method may also include determining a sleep stage for the individual by operating on the set of signal features using a sleep stage classifier included in a learning library. The sleep stage classifier may include a set of functions defining a likelihood that the individual is in the sleep stage based on the set of signal features.

Additional features and advantages of the disclosed embodiments will be set forth in part in the description that follows.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, may serve to explain the principles of the disclosed embodiments as set forth in the accompanying claims.

DETAILED DESCRIPTION

Figure 1:
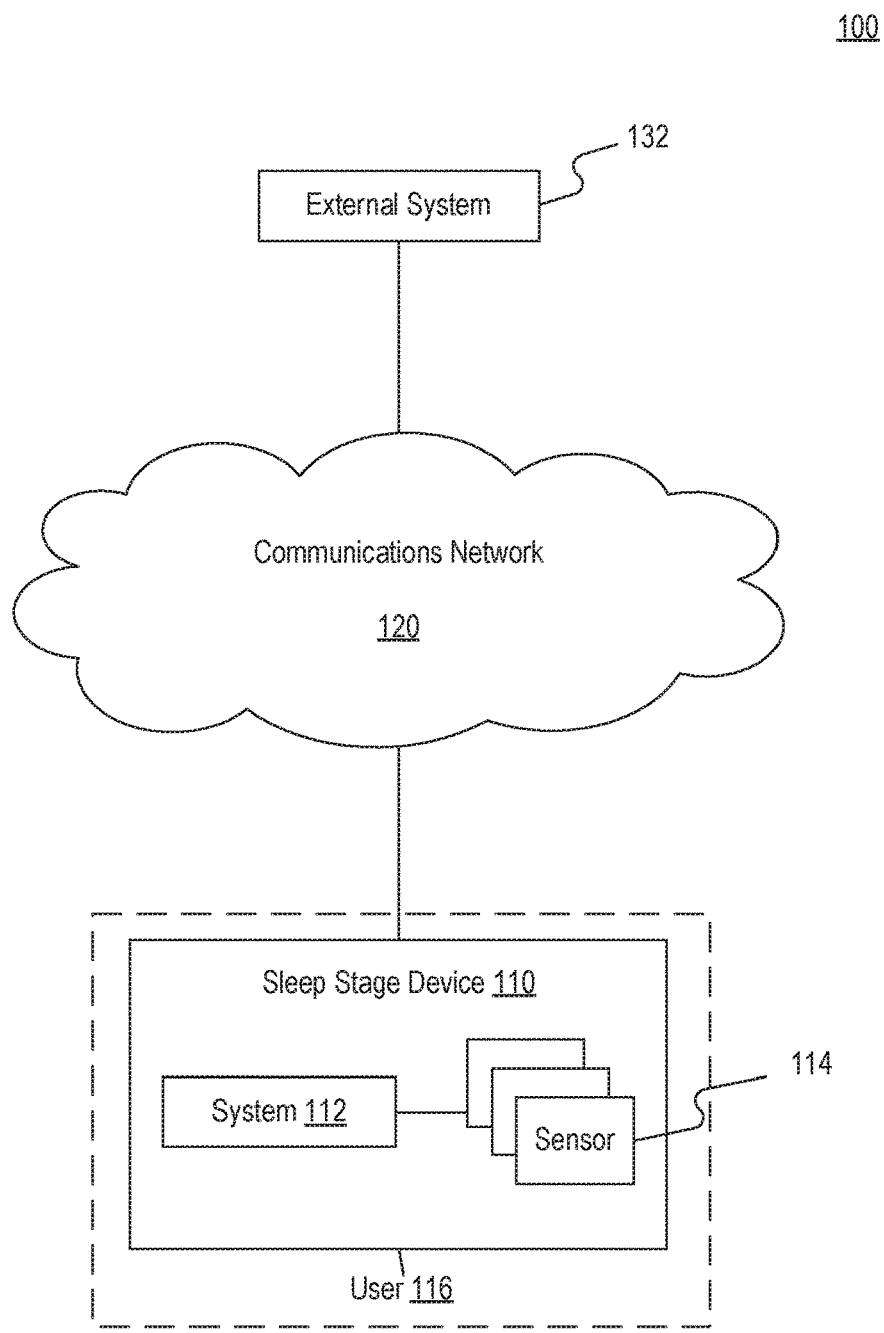
FIG. 1 depicts an example system environment for implementing embodiments consistent with the present disclosure.

The disclosed embodiments relate to systems and methods for probabilistically estimating an individual's sleep stage. As used herein, a sleep stage may refer to one or more phases or states of sleep, each recognized phase or state having particular physiological characteristic(s). These phases and states may be known in the art. For example, potential sleep stages may include states such as Awake, N1, N2, N3, N4, REM, non-REM (NREM). In some cases, a potential sleep stage corresponds to a single recognized phase or state. In some cases, a potential sleep stage corresponds to multiple recognized phases or states of sleep. For example, stages N1-N4 may collectively comprise a non-REM (NREM) sleep stage. In another example, stages N3 and N4 may constitute a single stage (e.g., a "N3"). Certain stages may be labeled, such as "deep sleep," "light sleep," or some other descriptive phrase.

In some aspects, the disclosed embodiments may obtain, measure, detect, or receive a set of signals, including a photoplethysmographic (PPG) signal and an accelerometer (e.g., motion) signal, from a set of sensors included in a device worn on the individual. The disclosed embodiments may analyze the measured signals to generate a set of signal features. Some signal features may be based on other signal features. The set of signal features may include any type of data derived from the measured signals. For example, the set of signal features may include beat-to-beat intervals based on the PPG signal, pulse rates, beat interval distributions, beat interval signals, spectrograms of the interval signals, and other features of the PPG signal described herein. In addition, the set of signal features may include motion signals from the accelerometer signal and other features of the accelerometer signal as described herein. Accordingly, a signal feature may comprise a dimension with a single data point or a dimension with one or more sets of data points. Thus, the term "set of signal features" may refer to the one or more features/dimensions included in the set or to the one or more data points included in the features/dimensions. In some aspects, the disclosed embodiments operate on the set of signal features using a sleep stage classifier included in a learning library to probabilistically determine a sleep stage associated with the individual. In some aspects, the set of signal features may include an interval signal. In some aspects, the sleep stage classifier may include a set of functions defining a likelihood that the individual is in a particular sleep stage, such as a sleep stage selected from among a set of potential sleep stages.

Providing probabilistic estimates of a sleep stage consistent with the disclosed embodiments may provide one or more technical advantages and improvements. For example, the disclosed embodiments may provide more accurate measurements of an individual's sleep stage without the need for additional equipment. Many known systems for measuring sleep stages require costly or cumbersome sensors, diodes, machinery, specialized data processing devices, etc. Furthermore, the disclosed embodiments may additionally improve the accuracy of such sleep stage measurements by incorporating information unique to users, incorporating information from several signal types, and the like. In addition, aspects consistent with the disclosed embodiments may provide indicia of abnormal sleeping behaviors and other physiological conditions. For example, the disclosed embodiments may be implemented to accurately identify abnormal sleep conditions. For example, the disclosed embodiments may identify Insomnia, Nocturnal Frontal Lobe Epilepsy, REM Behavior Disorder, and the like, despite never being trained with non-healthy participants.

Reference will now be made in detail to embodiments of the present disclosure, examples of which are illustrated in the accompanying drawings. Where possible, the same reference numbers will be used throughout the drawings to refer to the same or like parts.

FIG. 1 depicts an example system environment 100 for implementing embodiments consistent with the present disclosure. In some aspects, environment 100 may include one or more sleep stage devices (e.g., sleep stage device 110), which may be associated with one or more individuals (e.g., user 116). In some aspects, sleep stage device 110 includes one or more computing systems 112 for implementing processes consistent with the disclosed embodiments. The one or more computing systems 112 may be communicatively connected to a set of one or more sensors 114. Sensors 114 may be included within sleep stage device 110 (as depicted in FIG. 1) or may be external to the sleep stage device 110. Environment 100 may include one or more external computing systems (e.g., external system 132). One or more communications networks (e.g., communications network 120) may communicatively connect one or more of the components of environment 100.

Sleep stage device 110 may comprise any computing or data processing device consistent with the disclosed embodiments. In some aspects, for example, sleep stage device 110 may comprise a wearable device implemented with hardware components, sensors, and/or software applications running thereon for implementing the disclosed embodiments. In certain embodiments, sleep stage device 110 may incorporate the functionalities associated with a personal computer, a laptop computer, a tablet computer, a notebook computer, a hand-held computer, a personal digital assistant, a portable navigation device, a mobile phone, an embedded device, a smartphone, environmental sensor, and/or any additional or alternate computing device. Sleep stage device 110 may transmit and receive data across a communications network (e.g., network 120). As depicted in FIG. 1, network 120 is a wireless network, e.g., a WiFi network, cellular network including 3G or 4G, or other network appropriate for wireless data communication. Sleep stage device 110 may further implement aspects of the disclosed embodiments without accessing other devices or networks, such as network 120 or external device 132.

In certain aspects, sleep stage device 110 may be associated with one or more individuals, such as user 116. In one example, user 116 may wear sleep stage device 110 (e.g., around the user's wrist, leg, chest, etc.) to perform one or more processes consistent with the disclosed embodiments, such as that described with reference to FIGS. 1-9. For example, user 116 may use sleep stage device 110 to input information, receive information, display information, and transmit information to and from other components in system environment 100, such as the external system 132. This information may comprise any data consistent with the disclosed embodiments.

Sleep stage device 110 may include one or more computing systems 112 for processing, storing, receiving, obtaining, and/or transmitting information, such as computing system 200 described in connection with FIG. 2. In some aspects, system 112 may be implemented with hardware components and/or software instructions to perform one or more operations consistent with the disclosed embodiments (e.g., the example embodiments described with reference to FIGS. 1-9). The software instructions may be incorporated into a single computer or any additional or alternative computing device (e.g., a single server, multiple devices, etc.). System 112 may also include or associate with distributed computing devices and computing systems, and may execute software instructions on separate computing systems by remotely communicating over a network (e.g., communications network 120). System 112 may also implement aspects of the disclosed embodiments without accessing other devices or networks, such as communications network 120. Sleep stage device 110 and/or system 112 may also be implemented with one or more data storages for storing information consistent with the embodiments described below.

In some aspects, sleep stage device 110 may communicate with a set of sensors 114. Sensors 114 may measure individually or any combination of physical, temporal, geospatial, and/or environmental characteristic(s) associated with user 116. For example, sensors 114 may include one or more of an optical pulse rate monitor, optical blood pressure sensor, a GNSS receiver/transceiver, GPS receiver, accelerometer, gyroscope, thermometer, compass, posture sensor, hygrometer, pressure sensor, electrocardiogram, any polysomnography (PSG) sensor (e.g., electromyographs, electrodes, etc. for measuring EEGs, EOGs, ECGs, EMGs, etc.), blood-oxygen saturation sensor, clock, and/or other such sensor. Sensors 114 may measure characteristics internal to user 116 (e.g., the user's pulse rate, body temperature, blood pressure, etc.), external to user 116 (e.g., the ambient temperature, humidity, moisture levels, air pressure, barometric pressure, etc.), or otherwise associated with user 116 (e.g., the user's motion, location, speed, direction of travel, altitude, lateral or longitudinal acceleration, etc.). The set of sensors 114 may be implemented as hardware components within sleep stage device 110, reside external to the device, or some combination of the two. Preferably, sleep stage device 110 includes each sensor in the set of sensors 114.

In some aspects, sleep stage device 110 uses signals received from sensors 114 to determine or derive information associated with user 116. For instance, sleep stage device 110 may receive, measure, or detect a PPG signal associated with user 116 (e.g., via an optical pulse rate sensor). Sleep stage device 110 may detect and/or measure a user's 116 movement based on signals from an accelerometer. Sleep stage device 110 may determine a user's location based on GNSS/GPS measurements. Sleep stage device 110 may determine a posture associated with user 116 based on, for example, gyroscope measurements or a posture sensor. Sleep stage device 110 may determine a user's activity based on, for example, a determined speed associated with the user, the user's location, the user's posture, etc. Sleep stage device 110 may derive, detect, or determine any such information from sensors 114 consistent with the disclosed embodiments. As used herein, any sensor signal or other physical, temporal, or environmental characteristic derived therefrom (e.g., speed, acceleration, user activity, etc.) may be referred to as a signal, although such description is used for illustrative purposes only and is not intended to be limiting to the claims or this disclosure. For example, sleep stage device 110 may receive, detect, measure, and/or derive signals associated with a PPG signal, an accelerometer signal, a posture signal, a sleep stage signal, a blood pressure signal, signals associated with polysomnography (PSG) measurements such as EEG, EOG, or EMG signals, etc., signals associated with spectrograms of time-valued signals (e.g., a spectrogram of a PPG signal over time), transformations of such signals (e.g., an interval signal as described in connection with certain embodiments below), and/or any other type of signal measured by or derivable from a set of sensors 114.

Environment 100 may include one or more communications networks 120. In some aspects, communications network 120 may represent any type of communications network or medium of digital communication for transmitting information between computing devices. For example, network 120 may include a LAN, a wireless LAN, a cellular network, an RF network, a Near Field Communication (NFC) network (e.g., a WiFi network), a wireless Metropolitan Area Network (MAN) connecting multiple wireless LANs, NFC communication link(s), any physical wired connection (e.g., via an I/O port), and/or a WAN (e.g., the Internet). In some embodiments, communications network 120 may be secured through physical encryption (e.g., line encryption), by requiring information to be encrypted on other computer systems (e.g., end encryption), and the like.

In certain aspects, communications network 120 may include any accessible network or networks interconnected via one or more communications protocols, including hypertext transfer protocol (HTTP) and transmission control protocol/internet protocol (TCP/IP). Communications protocols consistent with the disclosed embodiments may also include protocols facilitating data transfer using radio frequency identification (RFID) communications and/or NFC. In some aspects, communications network 120 may also include one or more mobile device networks, such as a GSM network or a PCS network, allowing devices (e.g., sleep stage device 110) to send and receive data via applicable communications protocols, including those described herein.

Environment 100 may include one or more external systems (e.g., external system 132) for processing, storing, receiving, obtaining, and transmitting information. External system 132 may comprise any type of computing system consistent with the disclosed embodiments, such as computing system 200 of FIG. 2. External system 132 may be implemented with hardware components and/or software instructions to perform one or more operations consistent with the disclosed embodiments, such as those described with reference to FIGS. 2-9. The software instructions may be incorporated in a single system or may be distributed among several systems. In certain aspects, external system 132 may include one or more servers and/or one or more data repositories, memories, or other storages for storing and managing information. External system 132 may communicate information with one or more other components of environment 100 (e.g., sleep stage device 110, another external system 132, etc.) via one or more communications network 120.

In some aspects, external system 132 may reflect a computing system directly associated with, storing data for, hosting, or otherwise communicating with sleep stage device 110. Additionally or alternatively, external system 132 may reflect a computing system of an external entity not directly associated with sleep stage device 110, such as a computing system associated with a third-party business, governmental organization, educational institution, etc.

Figure 2:
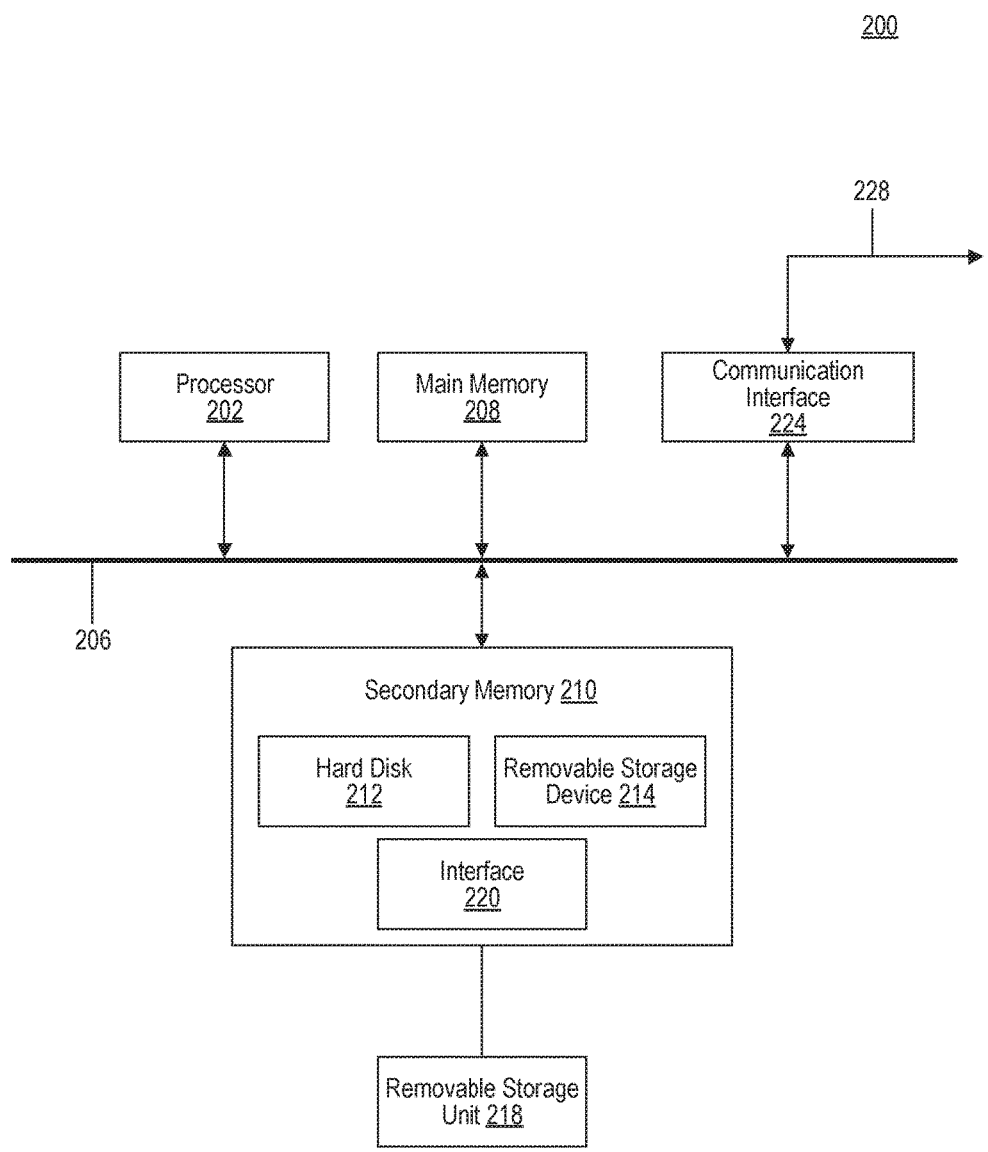
FIG. 2 depicts an example computing system consistent with the disclosed embodiments.

FIG. 2 depicts a block diagram of an example computer system 200 consistent with the disclosed embodiments. For example, in some aspects, computer system 200 may comprise computer systems associated with a device (e.g., sleep stage device 110, external system 132, etc.) performing one or more of the processes disclosed herein. In some embodiments, computer system 200 may include one or more processors 202 connected to a communications backbone 206 such as a bus or external communications network (e.g., any medium of digital data communication such as a LAN, MAN, WAN, cellular network, WiFi network, NFC link, Bluetooth, GSM network, PCS network, I/O connection, any wired connection such as USB or hardwired circuitry, and any associated protocols such as HTTP, TCP/IP, RFID, etc). Communications backbone 206 and/or one or more other components of computing system 200 may directly or indirectly communicatively connect the system to other components or peripherals, such as a set of sensors 114 (e.g., as implemented within sleep stage device 110).

In certain aspects, computer system 200 may include main memory 208. Main memory 208 may comprise random access memory (RAM) representing a tangible and nontransitory computer-readable medium storing computer programs, sets of instructions, code, or data executed with processor 202. When executed by processor 202, such instructions, computer programs, etc., may enable processor 202 to perform one or more processes or functions consistent with the disclosed embodiments. In some aspects, such instructions may include machine code (e.g., from a compiler) and/or files containing code that processor 202 may execute with an interpreter.

In some aspects, main memory 208 may also include or connect to a secondary memory 210. Secondary memory 210 may include a disk drive 212 (e.g., HDD, SSD), and/or a removable storage drive 214, such as a magnetic tape drive, flash memory, an optical disk drive, CD/DVD drive, or the like. The removable storage drive 214 may read from and/or write to a removable storage unit 218. Removable storage unit 218 may represent a magnetic tape, optical disk, or other storage medium that is read by and written to by removable storage drive 214. Removable storage unit 218 may represent a tangible and non-transitory computer-readable medium having stored therein computer programs, sets of instructions, code, or data to be executed by processor 202.

In other embodiments, secondary memory 210 may include other means for allowing computer programs or other program instructions to be loaded into computer system 200. Such means may include, for example, another removable storage unit 218 or an interface 220. An example of such means may include a removable memory chip (e.g., EPROM, RAM, ROM, DRAM, EEPROM, flash memory devices, or other volatile or nonvolatile memory devices) and associated socket, or other removable storage units 218 and interfaces 220, which may allow instructions and data to be transferred from the removable storage unit 218 to computer system 200.

Computer system 200 may also include one or more communications interfaces 224. Communications interface 224 may allow software and data to be transferred between computer system 200 and external systems (e.g., in addition to backbone 206). Communications interface 224 may include a modem, a network interface (e.g., an Ethernet card), a communications port, a PCMCIA slot and card, etc. Communications interface 224 may transfer software and data in the form of signals, which may be electronic, electromagnetic, optical or other signals capable of being received by communications interface 224. These signals may be provided to communications interface 224 via a communications path (e.g., channel 228). Channel 228 may carry signals and may be implemented using wire, cable, fiber optics, RF link, and/or other communications channels. In one embodiment, the signals may comprise data packets sent to or coming from processor 202. For example, computer system 200 may receive signals from a set of sensors (e.g., sensors 114) via communications interface 224 and/or communications backbone 206. Information representing processed packets may also be sent in the form of signals from processor 202 through communications path 228.

In certain aspects, the computer-implemented methods described herein may be implemented on a single processor of a computer system, such as processor 202 of computer system 200. In other embodiments, these computer-implemented methods may be implemented using one or more processors within a single computer system and/or on one or more processors within separate computer systems in communication over a network.

In certain embodiments, the terms "storage device" and "storage medium" may refer to particular devices including, but not limited to, main memory 208, secondary memory 210, a hard disk installed in hard disk drive 212, and removable storage unit 218 of FIG. 2. Further, the term "computer-readable medium" may refer to devices including, but not limited to, a hard disk installed in hard disk drive 212, any combination of main memory 208 and secondary memory 210, and removable storage unit 218, which may respectively provide computer programs and/or sets of instructions to processor 202 of computer system 200. Such computer programs and sets of instructions can be stored within one or more computer-readable media. In certain aspects, computer programs and sets of instructions may also be received via communications interface 224 and stored on the one or more computer-readable media.

The disclosed embodiments may include systems and methods for probabilistically determining an individual's sleep stage based on pulse rate information, such as heartbeat intervals measured in a PPG signal. The disclosed embodiments may also incorporate other information, such as motion data (e.g., as measured with an accelerometer), into its determinations. For example, the disclosed embodiments may analyze measured PPG signals and accelerometer signals to determine a set of beat intervals associated with the individual's pulse rate and motion information. The disclosed embodiments may use the beat intervals, raw PPG signals, motion data, and/or any other measured or derived data (e.g., the user's posture, orientation, etc.), to generate a set of signal features based on the measured signals. In some aspects, for instance, the disclosed embodiments may divide and/or partition a PPG signal into equally-timed segments, determine a beat interval or set of beat intervals associated with each segment, sample the set of beat intervals to generate an interval signal, and generate a spectrogram of the resulting interval signal. The disclosed embodiments may then operate on the generated set of signal features, including the spectrogram of the interval signal, time-averaged beat interval from raw PPG data, etc., using a sleep stage classifier included in a learning library. In some aspects, the sleep stage classifier may comprise a set of functions defining a likelihood that an individual is in a particular sleep stage (e.g., from among a set of potential sleep stages such as awake, NREM, REM, etc.) given a set of signal features. In certain aspects, the set of functions may include a set of signal weights derived from correlations between each feature in the set of features to known, previously-identified sleep stages associated with the training set learning library. This learning library may be constructed, maintained, and/or updated in any manner consistent with the disclosed embodiments.

Figure 3:
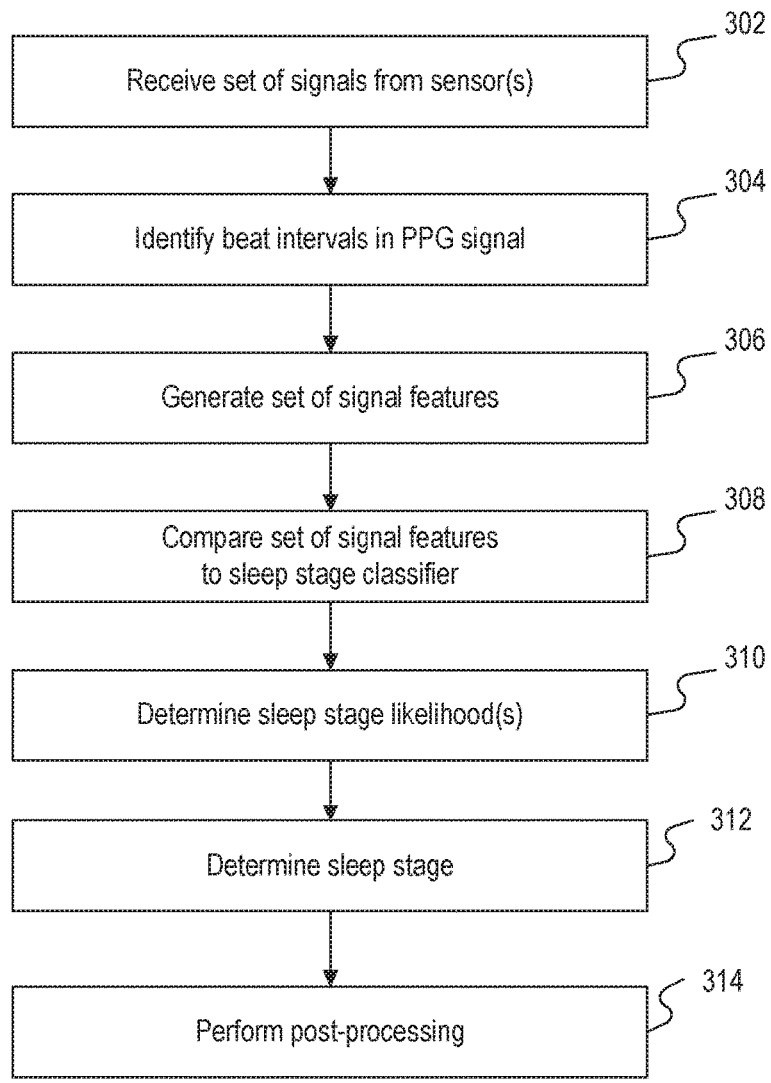
FIG. 3 depicts a flowchart for an example process for probabilistically estimating an individual's sleep stage consistent with the disclosed embodiments.

FIG. 3 depicts a flowchart for an example process 300 for probabilistically estimating an individual's sleep stage consistent with the disclosed embodiments. The example process 300 may be implemented via hardware and/or software instructions on one or more of the components of environment 100, such as sleep stage device 110, external system 132, or any combination thereof. Moreover, in certain aspects, process 300 may occur or be implemented as a standalone process. In other embodiments, process 300 may take place in the context of other processes. Certain aspects of process 300 may be reordered, rearranged, repeated, omitted, supplemented, modified, or integrated into additional processes in ways consistent with the disclosed embodiments.

The example process 300 of FIG. 3 begins by receiving a set of signals from a set of sensors 114 (step 302). The set of signals may include one or more signals consistent with the disclosed embodiments, such as a PPG signal measured with an optical heart rate sensor implemented on sleep stage device 110. In some aspects, the set of signals may include other signals consistent with the disclosed embodiments. For example, the set of signals may include an accelerometer signal (e.g., a motion signal) as measured with an accelerometer implemented in sleep stage device 110. In addition, the set of signals may include a posture signal (e.g., as measured by a posture sensor or derived from accelerometer and gyroscope sensors, etc.), a location signal, a speed signal, a temperature signal, or any other type of signal consistent with the disclosed embodiments. As part of step 302, sleep stage device 110 may receive these signals directly from the set of sensors 114 (e.g., as implemented within sleep stage device 110) and/or detect, measure, or otherwise derive them to form the set of signals described herein.

The set of sensors 114 may include one or more sensors consistent with the disclosed embodiments, such as an optical pulse rate sensor and accelerometer. In some aspects, the set of sensors may include one or more other sensors, such as a GNSS sensor, a GPS receiver, a thermometer, an air pressure sensor, a blood pressure sensor, or any other sensor contemplated by the disclosed embodiments (e.g., the types of sensors described with connection with FIG. 1).

In some aspects, process 300 may include identifying a set of beat intervals associated with a PPG signal in the set of signals (step 304). In some embodiments, a beat interval may reflect a duration of time between successive heartbeats reflected in the PPG signal measured with sleep stage device 110. Process 300 may determine the set of beat intervals by, for example, an Automatic Multiscale Pulse Detection (AMPD) algorithm to extract timings in peaks in the PPG signal. Additionally or alternatively, process 300 may determine a set of beat intervals by identifying local maxima in the PPG signal (e.g., based on a changing polarity of the first derivative of the PPG signal, ds/dt, the polarity of the second derivative, $d^2s/dt^2$, where s represents the PPG signal, etc.) having an amplitude exceeding a certain pulse threshold.

Process 300 may also determine a set of beat intervals by sampling the pulse rate associated with user 116 and taking the reciprocal of the time-averaged pulse rate to determine the beat interval. For example, a pulse rate of 80 BPM may be associated with a beat interval of 0.75 seconds. In this example, process 300 may generate a set of beat intervals by transforming a PPG signal measured over a period of time into the frequency domain (e.g., via one or more fast Fourier transforms (FFTs) or other suitable mathematical transform), determining the strength of the spectrum in the frequency domain, and inverting the frequencies corresponding to the local maxima exceeding a threshold to generate a time associated with the beat interval. In addition, process 300 may determine beat intervals through other known processes. Process 300 may thus use pulse rates to perform the same operations as those described in connection with beat intervals.

As contemplated herein, the set of beat intervals may reflect a single, time-averaged value of the beat interval (e.g., the reciprocal of the pulse rate) over a period of time. In this example, process 300 may determine the beat interval by averaging all identified beat intervals over a short time period (which may have a duration of, for example, up to one second, up to a few (e.g., 5) seconds, up to a minute, or any other sampling period, etc.), computing a moving and/or weighted average over a finite set of such prior averages or intervals, determining an average pulse rate (standard or moving) and computing its reciprocal, or any other measure consistent with the disclosed embodiments. In other aspects, the set of beat intervals may reflect a distribution or histogram of measured beat intervals so that the beat interval variability may be determined. For example, process 300 may measure a PPG signal over a time period, determine the time between successive heartbeats as described herein (e.g., by identifying peaks in the frequency and/or time domain), and generate a distribution or histogram of the beat intervals for that time period. Other methods and techniques may be implemented for determining the set of beat intervals consistent with the disclosed embodiments. For example, process 300 may determine the beat interval by generating a distribution of beat intervals and finding the beat interval associated with the maximum (e.g., mode) value of the distribution or histogram. Other statistical parameters, such as the median or mean, may also be used for this purpose. In some aspects, the set of beat intervals may be associated with a confidence interval for use in further processing (e.g., based on the mean and standard deviation of the beat interval distribution), although this confidence interval is not required.

In some embodiments, process 300 may include generating a set of signal features X based on a set of signals (step 306). In some aspects, a signal feature may reflect a signal, value, set of values, signal profile (e.g., waveform), distribution, and/or characteristic based on one or more signals (raw, derived, etc.). Process 300 may generate the set of signal features X using any process consistent with the disclosed embodiments, such as those described in connection with FIGS. 4-8. As described in greater detail below, for instance, process 300 may generate an interval signal by determining a set of beat intervals corresponding to equally-timed segments of a PPG signal and sampling the set of beat intervals at a particular/predetermined sampling rate (e.g., 1 Hz, 4 Hz, etc.). In some aspects, the interval signal may itself reflect a signal feature. Additionally or alternatively, the interval signal may be further processed to generate additional signal features, such as those described in reference with FIG. 4.

The set of signal features X may include features derived from signals other than a PPG signal. By way of illustration, process 300 may determine some signal features based on signals from an accelerometer, gyroscope, or other such sensor 114. In one example, for instance, process 300 may generate a signal feature by sampling an accelerometer signal at a particular/predetermined sampling rate (e.g., 25 Hz, 50 Hz, etc.). In this example, the raw accelerometer signal may comprise a three-dimensional vector reflecting detected motion of user 116 (in addition to other potential sources of acceleration). In some aspects, process 300 may differentiate the sampled accelerometer signal over each channel associated with the accelerometer signal (e.g., an x, y, and/or z axis, each axis in set of coordinate axes, etc.) to determine a rate of change of the individual's motion over each channel over time. Process 300 may also determine a time-averaged motion signal by averaging a magnitude of the differentiated accelerometer signals over a time window, such as 5, 10, or 20 seconds, etc. It will be apparent from this disclosure that other methods may be utilized for sampling, averaging, and aggregating the measured accelerometer signal, and the description above is for exemplary purposes only. Process 300 may include any of the foregoing parameters (e.g., the time-averaged motion signal, the differentiated accelerometer signal(s), the raw accelerometer signal, etc.) in the set of signal features. Other types of signal features will be apparent based on the above discussion and the description of other exemplary signal features below.

Given a set of signal features X, process 300 may include operating on the set of signal features using a sleep stage classifier (step 308). In some embodiments, a sleep stage classifier may reflect a set of functions, parameters, computational weights, etc., defining a likelihood that an individual is in a particular sleep stage based on a set of inputs such as signal features X and/or signals. For example, in one exemplary embodiment, the sleep stage classifier may reflect some set of logical and/or mathematical combination of signals or signal features defining a likelihood that an individual is in the REM sleep stage based on the set of signal features (e.g., an interval signal, a time-averaged motion signal, etc.). In some aspects, the set of functions in the sleep stage classifier may define a sleep stage likelihood $p_\phi(X)$ for each potential sleep stage $\phi$ in a set of potential sleep stages $\Phi$ (e.g., NREM, N1, N2, N3, REM, awake, etc.). In this example, the sleep stage likelihood $p_\phi(X)$ may reflect the likelihood that an individual is currently in a particular stage of sleep $\phi$ based on a set of signal features received or derived from a set of sensors 114. Given a set of signal features X, for example, the sleep stage classifier include a set of functions $f$ (which themselves may comprise a function or composite of functions as described below) such that $p_\phi(X) = f(X)$. In some aspects, the set of functions may be particularized to the potential sleep stage $\phi$ so that each stage corresponds to its own set of classification functions $p_\phi(X) = f_\phi(X)$. In these and other aspects, the set of functions comprising the sleep stage classifier may include one, several, or all such sets of stage-based functional representations $$\left(\text{e.g., } f(X) = \bigcup_{\varphi \in \Phi} f_\varphi(X)\right).$$

As described in greater detail below, the sleep stage classifier and its components (e.g., the set of functions and their component weights, operators, etc.) may be generated using processes consistent with the disclosed embodiments, such as those described in connection with FIGS. 4-8.

In some aspects, process 300 may determine a set of sleep stage likelihoods based on the comparison between the set of signal features or other inputs and sleep stage classifier(s) (step 310). In certain embodiments, the set of sleep stage likelihoods may include a single value reflecting the likelihood that an individual is currently in a particular stage of sleep (e.g., REM), p(X). In other aspects, the set of sleep stage likelihoods may comprise one or more such likelihoods $p_\phi(X)$, each reflecting the likelihood that the individual is in a respective sleep stage in a set of potential sleep stages (e.g., N1, N2, REM, etc.). Process 300 may generate the set of sleep stage likelihoods using processes consistent with the disclosed embodiments, such as the processes disclosed in connection with FIGS. 4-8. For example, process 300 may determine the likelihood that the individual is in the REM sleep stage based on a set of features derived from a PPG signal and an accelerometer signal.

Process 300 may include determining an individual's sleep stage based on a set of sleep stage likelihoods (step 312). Process 300 may determine this sleep stage in any manner consistent with the disclosed embodiments. In one aspect, for example, process 300 may determine that the individual's sleep stage corresponds to the sleep stage associated with the highest sleep stage likelihood, $\max\{p(\phi)\} \rightarrow \phi$, where $\phi$ is selected from the set of all possible sleep stages $\Phi$, a subset of such stages, a single stage, etc. In another example, process 300 may additionally or alternatively ensure that the most likely sleep stage (or any sleep stage) has a sleep stage likelihood exceeding a stage likelihood threshold $\max\{p(\phi)\} > T_{sl}$. This threshold may for example be 80% or higher, 60% or higher, 50% or higher, etc. In one illustrative embodiment, for instance, process 300 may compute the sleep stage likelihood associated with the REM sleep stage, $p_{REM}(X)$. In this example, process 300 may determine that the individual is in the REM sleep stage when $p_{REM}(X) > T_{sl} = 0.5$ and in the NREM sleep stage when $p_{REM}(X) < T_{sl} = 0.5$. Of course, the foregoing stage likelihood thresholds are merely exemplary, and the disclosed embodiments contemplate any suitable value for the stage likelihood threshold, the use of a different threshold values for the REM and NREM determinations, the calculation of other sleep stage likelihoods associated with other sleep stages (e.g., N1, N2), and so forth.

In a further example, process 300 may determine the sleep stage as a function of all of the sleep stages, with sleep stage likelihoods exceeding a second stage likelihood threshold (which may be equal to or different than a first stage likelihood threshold described previously), $f(p(\phi) > T'_{sl}) \rightarrow \phi$. Process 300 may further base the sleep stage on previously determined sleep stages or sleep stage likelihoods. For example, when no sleep stage likelihood exceeds a stage likelihood threshold, process 300 may assume the current sleep stage is the same as a previously determined sleep stage, weigh the current set of sleep stage likelihoods by those previously generated (e.g., by averaging them, computing a moving average of the last few such computations, etc.), determining whether the weighed sleep stage likelihoods exceed the stage likelihood threshold or doing so without subjecting the weighed likelihoods to the threshold, etc. It will be appreciated from this disclosure that further elaborations and/or combinations may be implemented for determining a sleep stage based on one or more sleep stage likelihoods consistent with the disclosed embodiments above and below.

In some aspects, process 300 may include conducting post-processing consistent with the disclosed embodiments (step 314). Such post-processing may include, for example, updating the learning library and/or sleep stage classifier such as using processes described in connection with FIG. 9. Alternatively or additionally, post-processing may include storing data in a computing system (e.g., within sleep stage device 110, information transmitted to external system 132, etc.). This stored data may include information associated with the set of signals, set of signal features, set of sleep stage likelihoods, estimated or determined sleep stages, or any other information consistent with the disclosed embodiments.

Figure 4:
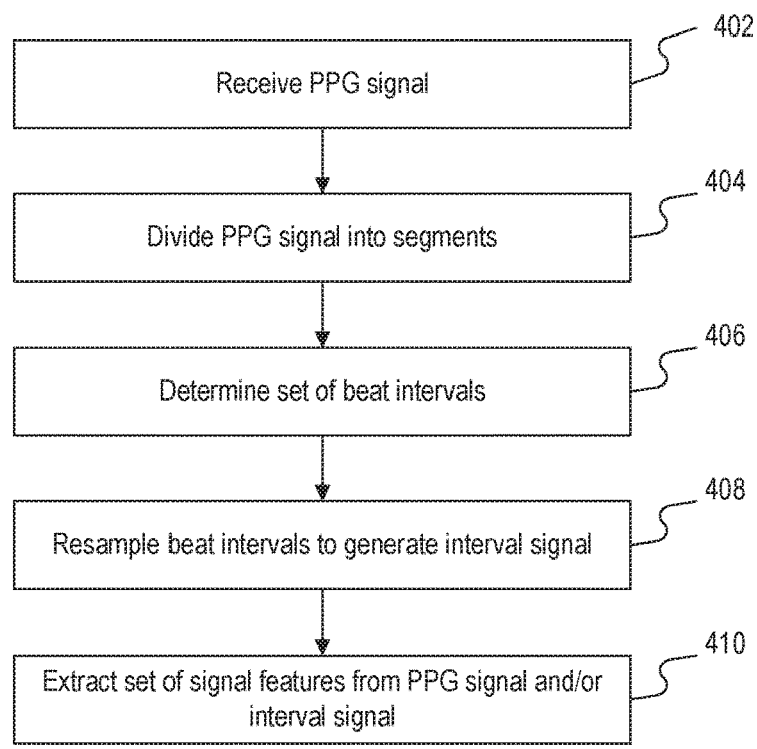
FIG. 4 depicts a flowchart for an example process for generating a set of signal features consistent with the disclosed embodiments.

FIG. 4 depicts a flowchart for an example process 400 for generating a set of signal features from an interval signal consistent with the disclosed embodiments. The example process 400 may be implemented via hardware and/or software instructions on one or more of the components of environment 100 such as sleep stage device 110, external system 132, or any combination thereof. Moreover, in certain aspects, process 400 may occur or be implemented as a standalone process. In other embodiments, process 400 may take place in the context of other processes, such as the sleep stage determination process of FIG. 3, or other processes. Certain aspects of process 400 may be reordered, rearranged, repeated, omitted, supplemented, modified, or integrated into additional processes in ways consistent with the disclosed embodiments.

Example process 400 begins by receiving a PPG signal, such as a PPG signal from an optical pulse rate sensor 114 implemented in sleep stage device 110 (step 402). The detected PPG signal may comprise any suitable PPG reading consistent with the disclosed embodiments. For example, the PPG signal may reflect a measure of light transmitted and/or reflected, e.g. by tissue of an individual, over time, e.g. as measured by a photodiode of sensors 114 (e.g., an optical pulse rate sensor). This measure may correspond to a volumetric measurement of blood in tissue and/or one or more organs of an individual. In certain aspects, process 400 may include determining whether the PPG signal received in step 402 comprises segments having equal time durations. If the received signal does not comprise segments having equal time durations, process 400 may include dividing the PPG signal into segments spanning one or more periods of time, such as 0.25, 1, or 4 seconds (step 404). Preferably, these periods of time are equally spaced and timed so that each segment spans the same timescale, but such uniformity is not required (e.g., the segments may reflect uniform or various period of time). In addition, process 400 may divide the PPG signal so that no segment overlaps with another (e.g., the segments form a partition or non-entire segmentation of the PPG signal) or that one or more segments overlap with one or more others for some small time period (e.g., a few milliseconds).

In certain aspects, if the PPG signal received in step 402 does comprise segments having equal time durations, process 400 may skip step 404 and proceed directly to step 406, as detailed below.

In some embodiments, process 400 may include measuring or otherwise determining a set of beat intervals for each of the segmented PPG intervals (step 406). The set of beat intervals may take any form consistent with the disclosed embodiments. In one example, for instance, the set of beat intervals may reflect an average beat interval measured over the PPG segment (e.g., the number of beats divided by the period of time elapsed by the time segment). In other aspects, the set of beat intervals may comprise other types of beat intervals consistent with the disclosed embodiments, such as a beat interval distribution, statistical characteristic of the measured beat intervals (e.g., median beat interval, mode beat interval, etc.), and the like.

Process 400 may include sampling the determined beat intervals at a particular/predetermined sampling rate (e.g., 1 Hz, 4 Hz, etc.) to generate an interval signal (step 410). In some aspects, the interval signal may reflect a last-measured beat interval (or statistical characteristic thereof) for every timestamp in the resampled domain. The interval signal may thus demonstrate/reflect how the measured beat intervals are changing over time. In certain aspects, the interval signal may comprise the sampled beat intervals (e.g., in milliseconds) measured at each resampled timestamp. For example, given a set of equally-timed PPG segments wherein each segment is associated with a beat interval, the interval signal may comprise a time-valued signal of these beat intervals (e.g., in ms) sampled at a specific rate (e.g., 4 Hz).

In some aspects, sampling the determined beat intervals may include sampling the intervals at the same frequency as that of the equally-timed PPG segments. For example, if the PPG segments each span a period of time, such as 0.25, 1, or 4 seconds, process 400 may include sampling the determined beat intervals at a frequency of 4, 1, or 0.25 Hz, respectively. In other aspects, sampling the determined beat intervals may include resampling the intervals at a frequency different than that of the equally-timed PPG segments. For example, if the PPG segments each span a period of time, such as 0.25, 1, or 4 seconds, process 400 may include sampling the determined beat intervals at a frequency not equal to 4, 1, or 0.25 Hz, respectively. Moreover, if the PPG segments are not representative of equal periods of time, process 400 may include resampling the determined beat intervals at a constant frequency.

In some embodiments, process 400 may include extracting one or more signal features from the interval signal and/or the underlying PPG signal (step 410). In one example, process 400 may derive or determine the raw, average pulse rate (e.g., the reciprocal of the beat interval) for the individual over a first period of time or sampling rate, such as every 4 seconds. In this example, process 400 may determine the average pulse rate for the individual using the raw PPG signal (e.g., using processes described herein), the segmented PPG signal (e.g., using the same types of processes), and/or the interval signal (e.g., by averaging the interval signal over the first time period and calculating its reciprocal). Process 400 may include this time-averaged pulse rate for the individual within the set of signal features for use in processes consistent with the disclosed embodiments.

In another example, process 400 may generate a set of spectrograms of the interval signal, each spanning one or more second period(s) of time. In these embodiments, the spectrograms may reflect the distribution of the interval signal transformed into the frequency domain. Process 400 may compute the spectrograms of the interval signal using processes described herein (e.g., an FFT or other suitable mathematical transform). The sampling rate or time period for the spectrogram (e.g., its width) may be the same as or different from the time period used for the time-averaged pulse rate signal feature. In one illustrative embodiment, for instance, process 400 may generate spectrograms of the interval signal having widths of 256 samples of the interval signal (e.g., approximately 1 minute for an interval signal sampled at 4 Hz). In some aspects, the spectrograms of the interval signal may be included in the set of signal features for use in processes consistent with the disclosed embodiments.

Additionally or alternatively, process 400 may include in the set of features one or more spectral power measurements determined from the spectrograms of the interval signal over certain frequency ranges or widths. In certain aspects, a spectral power measurement may reflect an amplitude or absolute energy of the spectrogram over a set of frequency widths, a frequency range, or some derivative value thereof. For example, in some embodiments, the set of spectral power measurements may reflect a sum of the absolute energy of the spectrogram in each of (or some or all of) a set of frequency bands comprising a very low frequency VLF (e.g., 0.01-0.04 HZ), a low frequency LF (e.g., 0.04-0.15 Hz), a high frequency HF (e.g., 0.18-0.40 Hz), and LF/HF. Of course, it will be readily apparent that other such frequency combinations and/or frequency ranges may be used for this purpose, and the listing of certain ranges is for exemplary purposes only. For example, in some embodiments, only one or three such bands may be used. In other embodiments, the listed frequency ranges may be adjusted, or other ratios of the power measurements may be used (e.g., HF/LF, VLF/LF, etc.).

Process 400 may include generating one or more additional signal features consistent with the disclosed embodiments, such as those described in reference to the accelerometer signal of FIG. 3. Alternatively, the foregoing set of signal features may be generated within a larger process (e.g., the signal feature generation step 306 of FIG. 3, step 508 of FIG. 5, step 608 of FIG. 6, other processes, etc.). As explained above, example process 400 may be incorporated into, or revised to include, other signal feature generation processes consistent with the disclosed embodiments. Accordingly, after generating these and other signal features, process 400 may terminate to enable the disclosed embodiments to conduct additional processing, such as the sleep stage determination process of FIG. 3, and so forth.

Figure 5:
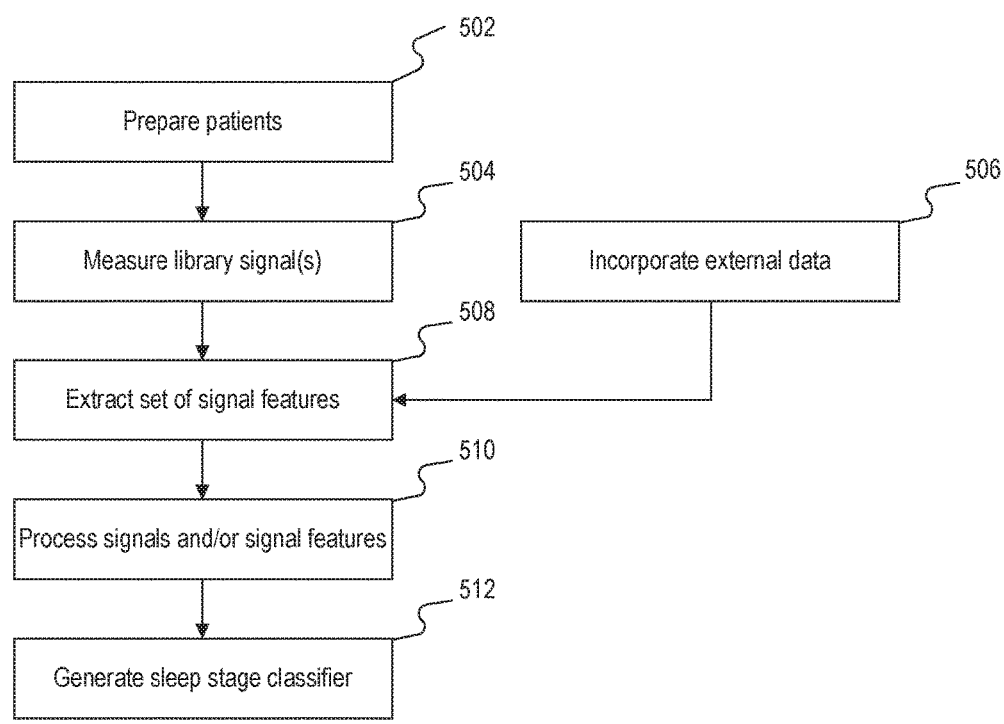
FIG. 5 depicts a flowchart for an example process for generating a sleep stage classifier from a learning library consistent with the disclosed embodiments.

FIG. 5 depicts a flowchart for an example process 500 for generating a sleep stage classifier from a learning library consistent with the disclosed embodiments. The example process 500 may be implemented via hardware and/or software instructions on one or more of the components of environment 100 such as sleep stage device 110, external system 132, or any combination thereof. Moreover, in certain aspects, process 500 may occur or be implemented as a standalone process. In other embodiments, process 500 may take place in the context of other processes, such as the sleep stage determination process of FIG. 3, or other processes. Certain aspects of process 500 may be reordered, rearranged, repeated, omitted, supplemented, modified, or integrated into additional processes in ways consistent with the disclosed embodiments.

Certain aspects of the disclosed embodiments may use a stored learning library to conduct some of its processes (e.g., the sleep stage determination process of FIG. 3). Referring back to FIG. 1, a learning library may be stored within computing system 112 of sleep stage device 110 and/or within external system 132. The library may also have at least a portion of its data stored within computing system 112 with the remaining portion stored within external system 132. In some embodiments, a learning library may comprise a set of stored training data wherein sets of signals (which may include, e.g., full sets of raw data, subsets of raw data, or other physical, temporal, or environmental characteristic (s) (e.g., speed, acceleration, user activity, etc.) derived from raw data), derived signal features, relevant classifiers, etc., are associated and correlated with known, accurate, previously-determined sleep stages (e.g., awake, N1-N4, REM, NREM, etc.) from polysomnography (PSG) measurements. These correlations may be used to generate a sleep stage classifier for use in other aspects (e.g., those described in connection with FIGS. 3, 7, 8, and other processes). Example process 500 is one illustrative embodiment for establishing the learning library.

Example process 500 begins by preparing a set of patients from whom the learning library will be constructed (step 502). In some embodiments, the set of patients may be a size suitable to generate statistically significant results (e.g., a sample size of about 25, 50, 100, or greater). The patients in the set of patients may exhibit normal sleeping habits or may alternatively experience sleeping abnormalities (e.g., such as Insomnia, Nocturnal Frontal Lobe Epilepsy, REM Behavior Disorder, Sleep Apnea, Bruxism, etc.). The inclusion of patients experiencing sleeping abnormalities may assist the disclosed embodiments in learning and providing processes for recognizing the physiological features of these disorders. Additionally or alternatively, the disclosed embodiments may incorporate these types of individuals using other clinical data, such as those described below. In either case, the disclosed embodiments have shown to identify, with reasonably accuracy, the presence of certain abnormal sleep conditions such as Insomnia, Nocturnal Frontal Lobe Epilepsy, and REM Behavior Disorder.

In certain aspects, process 500 may include measuring a set of library signals from each of the participants over a set of sleeping sessions (e.g., a night) (step 504). In some embodiments, the set of library signals may comprise a set of signals from which an individual's actual sleep stage $\phi$ may be accurately determined to a reasonable degree of certainty. The set of library signals may include any type of raw or derived signal consistent with the disclosed embodiments, such as those described in connection with various sensors or signals of FIGS. 1 and 3, or other such signal described herein. In one embodiment, for instance, the set of library signals may include EEG, EMG, and/or EOG measurements, other PSG measurements, a PPG signal, and/or an accelerometer signal from an accelerometer. By way of example, the library signal(s) may include one or more polysomnography measures such as an electroencephalogram EEG, an electrooculogram EOG, an electromyogram EMG, and/or an electrocardiogram ECG, etc. These library signal(s) may monitor the user's brain, eye, muscle, and heart activity, respectively, so that the individual's sleep stage may be accurately determined. Conventional methods and techniques may be used to determine an individual's sleep stage based on the EEG, EOG, EMG, and/or ECG signals. In this manner, process 400 may associate a known, accurate sleep stage $\phi$ to a concurrently measured set of signals (e.g., and/or their signal profiles or values) from a set of sensors 114. In the experimental study prepared prior to filed this application, for example, the set of library signals comprised EEG signals measured over three channels using a suitable device (e.g., an EEG sleep monitor such as a SleepProfiler device), a PPG signal (e.g., derived from a Study Kit wrist-worn device), and an accelerometer signal. The experimental study measured these signals from each participant over two consecutive nights, though other types and timings of sleeping sessions may be used. In general, the set of library signals need only include the signals necessary to derive an individual's sleep stage from physiological readings.

In some embodiments, process 500 may also incorporate external data into the library training set in lieu of or supplemental to that measured from the set of patients (step 506). In some aspects, the external data may include previously-measured laboratory data associating certain library signals (e.g., PSG readings such as ECG signals, PPG signals, etc.) with a known sleep stage $\phi$. In this manner, process 500 may expand the scale and breadth of the measurements extracted from the set of patients. This may enable the disclosed embodiments to increase the effective sample size of participants in the training data of the learning library, include participants with known sleep abnormalities into the training data set, and other such advantages. Because this external data may or may not be in the same form as the data measured in step 504, in some embodiments, process 500 may need to further process the external data to transform it into a form usable by the disclosed embodiments.

In some embodiments, step 506 may include incorporating patient data from a clinical database into the learning library to supplement the data thereof. The clinical database may contain, for example, multi-channel sleep data for patients collected in a sleep center. Further, the data may include recorded ECG signals for the patients. In some embodiments, pulse timestamps may be extracted from the recorded ECG signal using a Pan-Tompkins algorithm and the resulting measurements may be treated as training data as if they were measurements from a PPG signal. Further, if certain data like accelerometer data is not available, other signals may be used such as that from a chest belt measuring thoracic expansion. Such data may be filtered using a band-stop filter between, for example, 0.05 and 0.33 Hz (reflecting 3-20 respiration cycles per minute), resulting in frequencies correlating with abrupt motion in a similar manner as the motion detection measured from an accelerometer. The clinical database may include data from individuals with a variety of sleep conditions, such as insomnia, nocturnal frontal lobe epilepsy, REM behavior disorder, bruxism, and sleep apnea. Of course, the types of patients involved may vary depending on the source of data used.

Also, conventional methods or techniques may be used to convert or approximate certain forms of data into others to make them usable by the disclosed embodiments to conduct the processes and other features described herein.

After measuring the set of library signals and/or incorporating external data, process 500 may include extracting a set of signal features X from the set of signals and/or external data (step 508). Process 500 may extract these signal features using the processes consistent with the disclosed embodiments, such as those described in connection with FIGS. 3 and 4. For example, in one aspect, process 500 may extract an interval signal from PPG signals (or approximated PPG signals from external data) using the processes described above. In certain embodiments, process 500 may also determine the average pulse rate for the participants at a particular/predetermined sampling rate (e.g., 20 pulse windows over 4 second intervals). Process 500 may further compute spectrograms of the interval signal over certain time periods (e.g., 256 sampling widths of the interval signal) or calculate sums of the absolute energies in each of a set of frequency bands of the spectrograms (e.g., the VLF, LF, HF, and LF/HF bands). In some aspects, process 500 may determine a time-averaged motion signal from accelerometer or other motion data (e.g., as described in connection with FIG. 3).

Process 500 may include processing the input set of signals and/or extracted set of signal features X (step 510). This processing may include transforming the external data to a form usable by the disclosed embodiments, such as those embodiments described above. In addition, processing the signals and/or signal features may consist of other processes consistent with the disclosed embodiments, such as those described in connection with FIG. 6. In one example, for instance, process 500 may align, filter, and/or normalize the library signals, a set of signals measured from a set of sensors 114, and/or the set of extracted signal features. In other aspects, this processing may take place prior to extracting the set of signal features to ensure that the extract features reflect the processed data (e.g., data that is aligned, filtered, and/or normalized).

In some embodiments, process 500 may include generating a sleep stage classifier based on the set of signals and/or signal features X (step 512). In some embodiments, generating a sleep stage classifier may include generating, at least in part, the classifier recursively, i.e., with reference to previous classifiers within the learning library. Thus, generating a sleep stage classifier may involve known processes for machine learning. In a further embodiment, generating a sleep stage classifier may include generating, at least in part, the classifier with user supervision. In a still further embodiment, generating a sleep stage classifier may include generating, at least In part, the classifier using known deep learning processes, e.g., the process depicted in FIG. 8. Any of the preceding methods of generating a sleep stage classifier may be used in any combination thereof.

As explained above, the sleep stage classifier may comprise a set of functions defining a likelihood that an individual is in a particular sleep stage given a set of signals or signal features. Process 500 may generate the sleep stage classifier using any process consistent with the disclosed embodiments, such as those described in connection with the example processes and aspects of FIGS. 7 and 8. After generating the classifier, process 500 may terminate to allow for the disclosed embodiments to conduct other processes, such as those of the sleep stage determination process of FIG. 3, the library learning update process of FIG. 9, etc.

Figure 6:
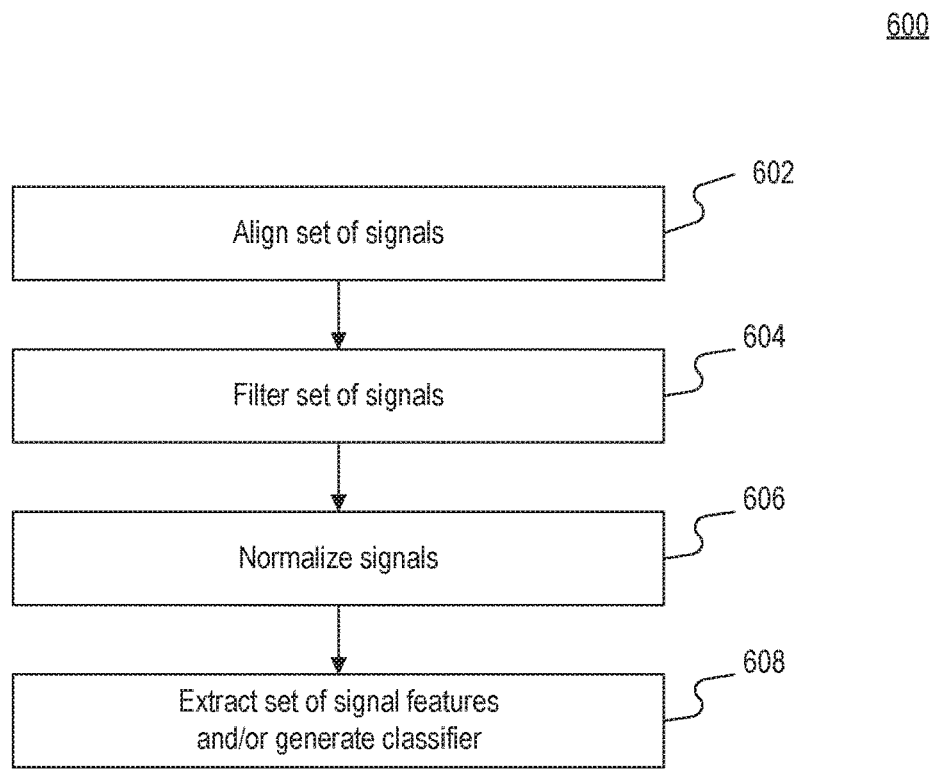
FIG. 6 depicts a flowchart for an example process for enhanced processing of a set of signals consistent with the disclosed embodiments.

FIG. 6 depicts a flowchart for an example process 600 for enhanced processing of a set of signals consistent with the disclosed embodiments. The example process 600 may be implemented via hardware and/or software instructions on one or more of the components of environment 100 such as sleep stage device 110, external system 132, or any combination thereof. Moreover, in certain aspects, process 600 may occur or be implemented as a standalone process. In other embodiments, process 600 may take place in the context of other processes, such as the sleep stage determination process of FIG. 3, the learning library or sleep stage classifier generation process of FIG. 5, or other processes. For example, processes consistent with those of example process 600 may be used to align, filter, normalize, or otherwise adjust a set of library signals (e.g., during a classifier generation process) and/or a set of signals obtained from a set of sensors 114 during a sleep stage estimation process. Certain aspects of process 600 may be reordered, rearranged, repeated, omitted, supplemented, modified, or integrated into additional processes in ways consistent with the disclosed embodiments.

In some aspects, process 600 begins by receiving and aligning a set of signals, such as a set of library signals received in a sleep stage classifier generation process (step 602). In certain embodiments, such an alignment may be necessary to account for different clock or timing offsets in the various sensors 114 used to measure the set of signals (e.g., an accelerometer signal, the PPG signal, an EEG signal, a sleep stage signal, etc.). In some aspects, process 600 may align the sets of signals by cross-correlating one signal with another and determining a distribution of offset delays between the signals.

For example, in one illustrative embodiment, process 600 may cross-correlate an EEG signal (e.g., from an EEG sleep monitor such as a SleepProfiler) with a PPG signal (e.g., from a Study Kit CAM) and determine a proportion of agreement in the estimated pulse rate among the two signals to determine the offset delay. In some embodiments, one or both of the input signals may be interpolated prior to performing the cross-correlation to render the signals suitable for cross-correlation (e.g., to account for different sampling rates between the two signals by incorporating the greatest common divisor and/or lowest common multiple of the two rates). In addition, determining the proportion of agreement may be done in an iterative manner using a set of offsets narrowing over time so that each iteration tightens the sampling interval and improves computation speed. Other types of computational considerations will be readily apparent based on the disclosed embodiments. For example, in another exemplary aspect, the timing offsets (e.g., for each sensor 114 or signal in the set of signals) may have a known or previously-determined clock offset, in which case process 600 may align the signals without performing the foregoing cross-correlation. Once process 600 determines an appropriate offset between two signals, process 600 may align the signals (e.g., shift one or both of the signals) with one another so that their readings correspond to the same moment in time and/or reflect the same physiological responses.

In certain embodiments, process 600 may further align the signals so that the signals or derived signal features are properly windowed. In some aspects, process 600 may undertake this alignment procedure to ensure that the signals and/or the derived set of features (e.g., an interval signal, spectrogram thereof, motion data, sleep stage signal, or other feature) correspond to the same moment in time and can be compared or associated with one another. In one embodiment, for example, 600 may align the signals (e.g., a PPG signal, an EEG signal, a pulse rate signal, etc.) so that the spectrograms are timed in uniform or known increments, such as one minute (e.g., roughly 256 samples in a sampled PPG signal at 4 Hz). Process 600 may also create an overlap period so that the signals can be properly aligned with one another. In one example, the overlap period of the spectral data may be set to 4 or 16 samples of the transformed PPG signal or interval signal when sampled at 4 Hz. Other windows are possible based on, for example, the underlying sampling rate(s). Process 600 may then align the signals by trimming the interval signal at the beginning of its segment by the determined overlap period so that the interval signal properly aligns with, for example, a sleep stage signal (e.g., as derived from a sensor 114 during a sleep stage classifier creation process) or other signal.

In an exemplary embodiment, process 600 may store a REM/NREM label calculated from three consecutive labels from an EEG sleep monitor (such as a SleepProfiler) as the known sleep stage for an individual. The EEG sleep monitor (such as a SleepProfiler) signal may provide these REM/NREM labels every 30 seconds (or other predetermined period). Process 600 may then store processed accelerometer data at 15 windows sampled every 2 seconds from both sides of the REM/NREM label (e.g., the sleep stage signal). Process 600 may further store averaged pulse rate information for 20 windows over 4 second periods on both sides of the REM/NREM label. The process may also store the summed energy from the each of the four frequency bands of spectral pulse rate information (over the VLF, LF, HF, and LF/HF bands) at 11 windows with the REM/NREM label in the middle. The spectral data (sampled at 1 minute windows with an overlap period of 16 samples) may be stored at 5 windows with the REM/NREM label in the middle such that each window contained 97 frequency components from 0-1.5 Hz. In this example, the average offset delay between the Study Kit CAM and Sleep Profiler signals was 34.4 seconds.

Process 600 may include filtering the aligned set of signals (step 604). In some aspects, process 600 may filter a set of signals based on, for example, a pulse rate quality factor associated with the pulse rate signal(s) within the set of signals. In some aspects, a pulse rate quality factor may reflect the reliability of the pulse rate measurements associated with the input pulse rate signals over a given/predetermined period of time. In some aspects, the pulse rate quality factor may arise as a function of the difference between the mean pulse rate as measured by one input signal (e.g., a PPG signal, which may, for example, be obtained from a Study Kit) and another input signal (e.g., an EEG signal as measured from an EEG sleep monitor such as a SleepProfiler). In this example, the pulse rate quality factor may be directly proportional to the difference in these mean pulse rates from the various input signals. In addition, the pulse rate quality factor may be based on whether an identified pulse rate falls outside, remains within, or approaches the boundary of, a physiological pulse rate interval. For example, process 600 may reduce the pulse rate quality factor for pulse rates associated with beat intervals falling outside or approaching the boundaries of the span of about 370-1700 ms (approximately 35-162 BPM), or other such suitable interval (e.g., 40-150 BPM). Process 600 may further base the pulse rate quality factor on other parameters such as, for example, the standard deviation, variance, or variability of one or more of the pulse rate signal(s) over one or more time periods. In one embodiment, for instance, process 600 may associate widely-varying pulse rates with lower pulse rate quality factors so that the pulse rate quality factor is inversely proportional to the variability of the underlying pulse rate signal.

In some embodiments, process 600 may exclude data points (e.g., segments of the PPG and EEG signals and the signal values associated with other signals during this time period) when the pulse rate quality factor falls below a quality threshold. Alternatively, process 600 may exclude these data points when other conditions are met (e.g., the mean difference between beat interval signals exceeds a threshold such as 50 ms, the pulse rates fall outside an acceptable physiological range, the variability of the underlying signal exceeds a threshold, etc.).

Process 600 may include normalizing a set of signals or signal features on a per-individual, per-sleep-session, per-channel, per-signal, and/or per-feature basis (step 606). In some aspects, for instance, normalizing a set of signals or features may include generating a normal distribution for the signal and/or feature in each channel for a given individual. In certain aspects, process 600 may reduce the impact of outliers in the measurements by using the median of the signal values at the central point of the normal distribution instead of its mean (e.g., because outliers affect a mean more prominently than the median). In some aspects, process 600 may calculate the standard deviation or variance of the normal distribution of the normalized signal or feature based on the median rather than the mean. In addition, process 600 may include other functions to transform the underlying signals or features, such as applying a logarithmic function (e.g., log( ) etc.) to whiten the data of each channel of a spectrogram, spectral power signal, or other signal relying on an exponential of an input.

In some aspects, process 600 may include extracting or generating a sleep stage classifier based on the normalized signals (step 608). In one example embodiment, for instance, process 600 may extract a set of signal features or generate a sleep stage classifier consistent with the embodiments described in connection with FIGS. 3-5, 7, and 8 based on a normalized, filtered, and/or aligned set of signals in a learning library. Process 600 may generate the set of signal features or sleep stage classifier in any manner consistent with the disclosed embodiments.

Figure 7:
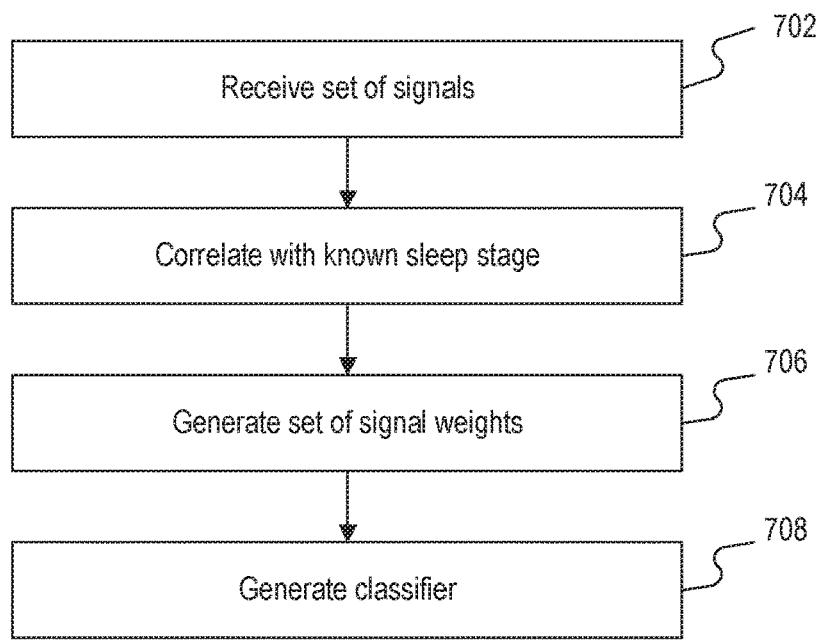
FIG. 7 depicts a flowchart for an example process of generating signal weights in a sleep stage classifier consistent with the disclosed embodiments.

FIG. 7 depicts a flowchart for an example process 700 of generating signal weights in a sleep stage classifier consistent with the disclosed embodiments. The example process 700 may be implemented via hardware and/or software instructions on one or more of the components of environment 100 such as sleep stage device 110, external system 132, or any combination thereof. Moreover, in certain aspects, process 700 may occur or be implemented as a standalone process. In other embodiments, process 700 may take place in the context of other processes, such as the sleep stage determination process of FIG. 3, the learning library or sleep stage classifier generation process of FIG. 5, or other processes. For example, in one aspect, process 700 may occur within processes consistent with establishing a learning library and sleep stage classifier associated therewith. Certain aspects of process 700 may be reordered, rearranged, repeated, omitted, supplemented, modified, or integrated into additional processes in ways consistent with the disclosed embodiments.

Example process 700 begins by receiving a set of signals and/or a set of signal features X, such as those measured, determined, or derived in the processes described in connection with FIGS. 3-6 (step 702). The set of signals or signal features may comprise any signal or signal feature consistent with the disclosed embodiments, such as a PPG signal, an interval signal, a spectrogram or energy analysis thereof, an accelerometer signal, etc. In certain aspects, process 700 may correlate the set of signals and/or the set of signal features with a known sleep stage (step 704). This known sleep stage may be determined, for example, based on PSG measurements including a sleep stage signal, multi-channel EEG signals, or other set of signals consistent with the disclosed embodiments (e.g., signals consistent with the learning library generation process of FIG. 5).

Process 700 may use a set of signal features and their correlation with a known sleep stage to create, generate, or define a sleep stage classifier. As explained above, for instance, a sleep stage classifier may comprise a set of logical and/or mathematical functions defining a likelihood that an individual is in a particular sleep stage based on a set of inputs such as a set of signals or signal features. In these aspects, the sleep stage classifier or its component functions may reflect a representation of a sleep stage based on a set of signal features. For example, given a set of signal features X, a sleep stage classifier may comprise a set of functions $f$ defining the relationship $p_\phi(X)=f(X)$.

In some aspects, the set of functions may comprise a single function taking any form consistent with the disclosed embodiments. In one example, for instance, the sleep stage classifier may comprise a linear combination of signal feature inputs, wherein each signal feature $x_i$ is weighted by a respective signal weight $\omega_i$:

$$p_\phi(X) = \sum_i \omega_i x_i.$$

In some aspects, a signal weight may reflect the relative importance or significance (or lack thereof) of a signal or signal feature in specifying an individual's sleep stage. These signal weights (as well as the underlying function f) may be predetermined or determined heuristically, empirically, or otherwise established by a computing system using the disclosed embodiments. The signal weights may exhibit ranges concomitant with the underlying expression for the sleep stage likelihood, such as [0,1], [−1,1], etc.

In one aspect, for example, process 700 may determine the values of the signal weights based on the measured correlations between a signal feature in the learning library and a known sleep stage φ (step 706). For example, process 700 may determine the values of the signal weights using a softmax function governing a set of normalized signal feature inputs. Given a set of sample features X having K dimensions, for instance, the probability for the i-th class may be given by $$p(x = i|X) = \frac{e^{X^T \Omega_i}}{\sum_{k=1}^{K} e^{X^T \Omega_k}}$$

where T represents the transpose operator. The values of the signal inputs may be based all or a subset of individuals and/or sleep sessions from the data in the learning library.

Of course, it will be readily apparent that the foregoing expression of the sleep stage classifier is merely exemplary. For example, the sleep stage classifier may instead be represented as a product of signals and their signal weights (e.g., $p_\phi(X)=\Pi_i \omega_i x_i$), as a multivariate polynomial function wherein each signal feature has a corresponding signal weight and power (e.g., $p_\phi(X)=\Sigma_i \omega_i x_i^{b_i}$), some statistical analysis of the set of signals (e.g., a multivariable regression analysis), any combination of these considerations, etc. Thus, the sleep stage classifier may be expressed as a function of its component input signal features X so that $p_\phi(X)=f(X)$ and the values of the signal weight(s) are governed by the softmax function.

In certain embodiments, the set of functions may include a composite of the foregoing functions, each associated with its own signal weight(s), collectively comprising a set of signal weights. In these embodiments, the sleep stage classifier may be expressed as a series of nested functions, each having their own expression and signal weights so that $p_\phi(X)=f(X)=f_1(f_2(\ldots f_n(X)))$. Process 700 may generate the expressions and signal weights associated with these functions in the same manner as described above. Additionally or alternatively, process 700 may determine the values of the signal weights of the intermediate (hidden) functions using the sigmoid activation function $$S(\omega) = \frac{1}{1+e^{-\omega}}$$

and an L2 weight decay $$L = \sum_i \omega_i^2$$

to suppress large weight values. In addition, process 700 may implement a dropout fraction (e.g., 0.15) to prevent overfitting of the signal weights.

By way of example, in an experimental study many neural network architectures were tested using two or three hidden layers using sigmoid activation functions except for the final output layer (function). The final output function instead used the softmax function to output the sleep stage likelihood. The system mapped 629 features in total, employed an L2 weight decay and dropout fraction of 0.15 to prevent large and overfitting signal weights. The training data was subjected to the network in batches of 20 with randomized epochs between 35 and 65.

Once process 700 determines the values for each of the signal weights, process 700 may thereby generate the sleep stage classifier, including the component signal weights and/or underlying functions for the sleep stage likelihood (step 708). The sleep stage classifier may then be implemented in the other processes consistent with the disclosed embodiments, such as the sleep stage estimation process of FIG. 3. Process 700 may then terminate to enable further processing consistent with the disclosed embodiments.

Figure 8:
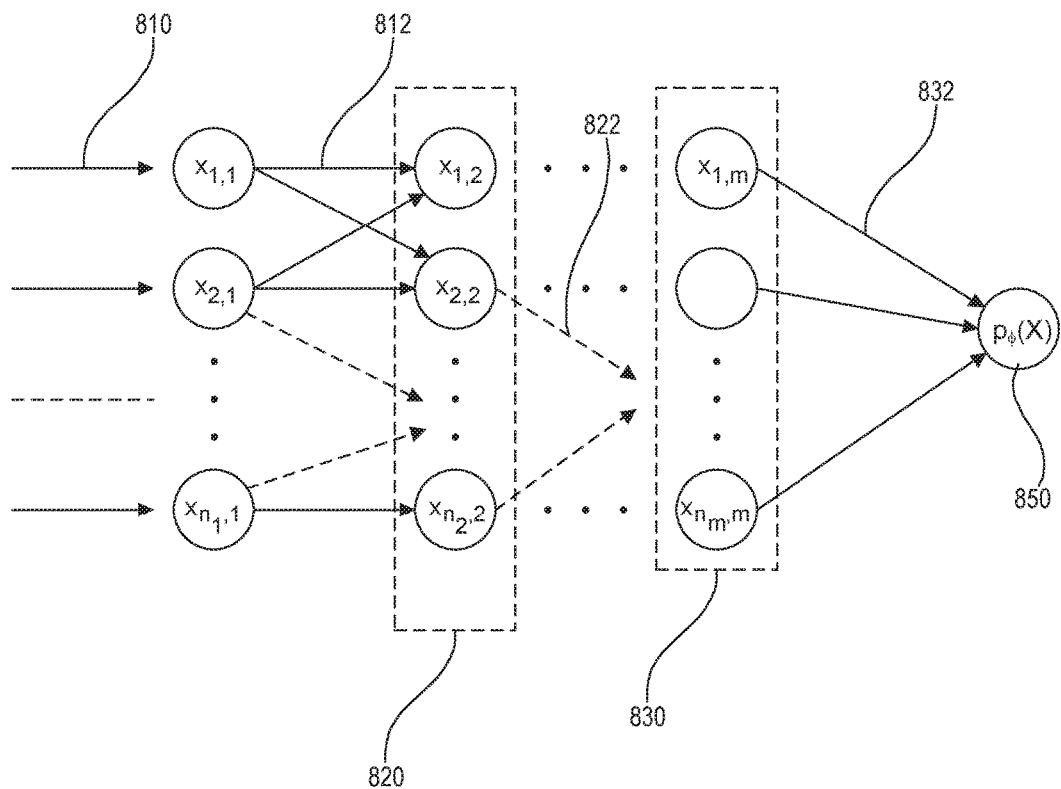
FIG. 8 depicts a block diagram of an example neural network consistent with the disclosed embodiments.

FIG. 8 depicts block diagram of an example neural network for determining signal weights consistent with the disclosed embodiments. The example diagram of FIG. 8 depicts one manner in which determining the signal weights may be conducted in the processes described in connection with FIG. 7 (e.g., assuming no dropout). In some aspects, for instance, the sleep stage classifier may receive a set of signal features 810 as inputs. The set of signal features 810 may contain $n_1$ number of such features so that the value of each feature is $x_{1,1}, x_{2,1}, \ldots, x_{n1,1}$. In some aspects, the sleep stage classifier may contain any number of hidden layers 820 and 830 (e.g., nested functions), including no such hidden layers. These hidden layers may have a respective number of intermediate values $n_2, \ldots, n_m$, which may be the same or different from each other and $n_1$. The sleep stage classifier may relate one function to another (e.g., one layer to another) via a set of signal weights 812 and 822 governing, for example, how a value like $x_{1,1}$ relates to a set of intermediate values $x_{1,2}, \ldots, x_{n2,2}$. These weights may be determined numerically via the sigmoid activation functions with L2 weight decay as described above, and may also be subjected to a dropout fraction (not shown). Once all of the intermediate layers and functions have been fitted, process 700 may employ a softmax function to determine a final set of signal weights 832 and generate the sleep stage probability $p_\phi(X)=f(X)$, 850.

Figure 9:
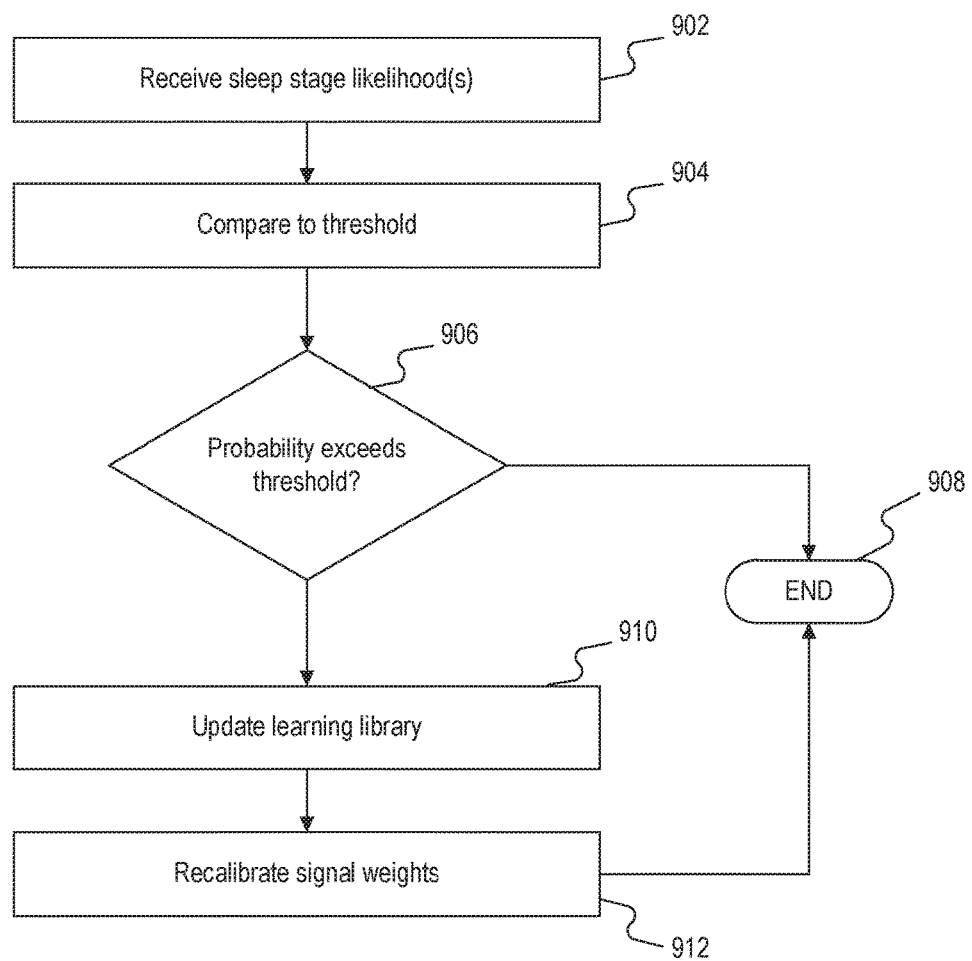
FIG. 9 depicts a flowchart for an example process for updating a learning library based on user data consistent with the disclosed embodiments.

FIG. 9 depicts a flowchart for an example process 900 for updating a learning library based on user data consistent with the disclosed embodiments. The example process 900 may be implemented via hardware and/or software instructions on one or more of the components of environment 100, such as sleep stage device 110, external system 132, or any combination thereof. Moreover, in certain aspects, process 900 may occur or be implemented as a standalone process. In other embodiments, process 900 may take place in the context of other processes (e.g., the probabilistic sleep stage estimation process 300 described in connection with FIG. 3). Certain aspects of process 900 may be reordered, rearranged, repeated, omitted, supplemented, modified, or integrated into additional processes in ways consistent with the disclosed embodiments.

Process 900 begins by receiving a set of sleep stage likelihoods, such as those determined in the processes consistent with FIGS. 3-8 (step 902). Each sleep stage likelihood may be associated with a particular potential sleep stage (e.g., REM, NREM, etc.). In some aspects, process 900 may include comparing each sleep stage likelihood to a user classification threshold (step 904). In some embodiments, the user classification threshold may be equal to and/or greater than the stage likelihood threshold(s) described in connection with FIG. 3.

If none of the sleep stage likelihoods exceed the user classification threshold (step 906; no), process 900 may terminate to enable the disclosed embodiments to conduct further processing (e.g., such as the processes described in connection with FIGS. 3-8) (step 908). For example, process 900 may terminate and the disclosed embodiments, may initiate process 300 by measuring a set of signals from a set of sensors 114.

If one or more sleep stage likelihoods exceed the user classification threshold (step 906; yes), process 900 may update the learning library and/or a sleep stage classifier for use in further processing (step 910). In some aspects, updating the learning library may comprise adding to the learning library the set of signals, signal features, sleep stage(s), etc., having a sleep stage likelihood exceeding the user classification threshold. Process 900 may associate the set of signals or signal features to all sleep stage(s) exceeding the user classification threshold in this manner or, alternatively, may limit such association to the sleep stage corresponding to the most likely sleep stage (e.g., having the highest sleep stage likelihood). In these embodiments, process 900 may consider a sleep stage having a probability exceeding the user classification threshold as a known sleep stage, despite not being measured by a full spectrum of PSG sensors. By including the set of signals and its associated sleep stage to the learning library, process 900 may thus incorporate signal profiles, signal features, and metrics specific to user 116 into the learning library so that, over time, the learning library adjusts to the user's specific body mechanisms, routines, and other physiological idiosyncrasies. This process enables the learning library to become unique to user 116.

In some aspects, process 900 may include updating a sleep stage classifier in response to an update to the learning library (step 912). For example, introducing new data points to the learning library (e.g., as a set of new signal features, known sleep stage, etc.) may alter the expressions for the functions comprising the sleep stage classifier and/or their component signal weights. Process 900 may recalculate all of the signal weights, functional expressions, or any other metric using the foregoing embodiments (e.g., using processes described in connection with the example embodiments herein, such as that of FIGS. 3-8). In this manner, process 900 may update the learning library to account for sets of signals, sets of signal features, and sleep stages specific to user 116 for use in subsequent calculations. Over time, the learning library (and thereby the sleep stage classifier) may thus reflect measurements and signal profiles unique to the user, improving the accuracy and validity of estimated sleep stages. Once process 900 has updated the learning library and recalibrated its corresponding parameters (e.g., classifiers, signal features, signal weights, etc.), process 900 may terminate (step 908) to enable for further processing consistent with the disclosed embodiments.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware and software, but systems and methods consistent with the present disclosure can be implemented as hardware alone.

Computer programs based on the written description and methods of this specification are readily within the purview of a software developer. The various programs or program modules can be created using a variety of programming techniques. For example, program sections or program modules can be designed in or by means of Java, C, C++, assembly language, or any such programming languages. One or more of such software sections or modules can be integrated into a device system or existing communications software.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Furthermore, unless otherwise indicated, the use of the phase "based on" is inclusive rather than exclusive. That is, a notation that one variable is based on another variable is intended to convey that the first variable is based at least in part on the second variable. Therefore, the phrase "based on" is intended in an open-ended sense.

Similarly, unless otherwise indicated, a "set" may include one or more member objects. That is, a notation of "a set of objects" is intended to convey that the set includes one or more objects.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed:

1. A method for probabilistically determining an individual's sleep stage, the method comprising the following operations performed via one or more processors:
   receiving a set of signals from a set of sensors worn by the individual, the set of signals including a photoplethysmographic (PPG) signal and an accelerometer signal;
   dividing the PPG signal into a set of equally-timed segments if the received PPG signal comprises segments having unequal time durations;
   determining a beat interval associated with each segment, the beat interval reflecting an elapsed time between successive heartbeats;
   sampling the set of beat intervals to generate an interval signal;
   generating a set of signal features based on the interval signal and the accelerometer signal, the set of signal features including a spectrogram of the interval signal; and
   determining a sleep stage for the individual by operating on the set of signal features using a sleep stage classifier included in a learning library, wherein the sleep stage classifier comprises a set of functions defining a likelihood that the individual is in the sleep stage based on the set of signal features.

2. The method of claim 1, wherein sampling the set of beat intervals comprises sampling using the frequency of the equally-timed segments.

3. The method of claim 1, wherein sampling the set of beat intervals comprises resampling using a frequency different from the frequency of the equally-time segments.

4. The method of claim 1, wherein the set of functions includes signal weights, and wherein each signal weight is based on a correlation between a feature in the set of signal features and a known sleep stage.

5. The method of claim 4, further comprising:
   sampling the accelerometer signal at a first sampling rate;
   differentiating the sampled accelerometer signal over each channel associated with the accelerometer signal; and
   averaging a magnitude of the differentiated accelerometer signals over an accelerometer time window to generate a time-averaged motion signal;
   wherein the set of signal features further comprises the time-averaged motion signal such that the sleep stage is further based on the time-averaged motion signal.

6. The method of claim 5, wherein the learning library comprises data from among a plurality of sessions for a plurality of individuals, and wherein the set of signal weights is based on normalizing each feature in the set of features over each session for each of the plurality of individuals.

7. The method of claim 4, wherein the set of signal features further comprise an average pulse rate derived from the PPG signal sampled at a second sampling rate and a sum of the absolute energy in each of a plurality of frequency bands in the spectrogram of the interval signal.

8. The method of claim 7, wherein the sleep stage is determined from among a set of potential sleep stages, wherein the set of potential sleep stages comprises an awake stage, a non-REM stage, and a REM stage, and further comprising determining a sleep stage likelihood for each of the potential sleep stages based on the set of signal features and the set of signal weights in the sleep stage classifier.

9. The method of claim 8, wherein determining the sleep stage further comprises:
identifying a most likely sleep stage based on a highest sleep stage likelihood among a set of sleep stage likelihoods including each sleep stage likelihood associated with a potential sleep stage; and
determining whether the highest sleep stage likelihood exceeds a preset stage likelihood threshold.

10. A system for probabilistically determining an individual's sleep stage, comprising:
a memory storing instructions; and
one or more processors configured to execute the instructions to perform one or more operations, the operations comprising:
receiving a set of signals from a set of sensors worn by the individual, the set of signals including a photoplethysmographic (PPG) signal and an accelerometer signal;
dividing the PPG signal into a set of equally-timed segments if the received PPG signal comprises segments having unequal time durations;
determining a beat interval associated with each segment, the beat interval reflecting an elapsed time between successive heartbeats;
sampling the set of beat intervals to generate an interval signal;
generating a set of signal features based on the interval signal and the accelerometer signal, the set of signal features including a spectrogram of the interval signal; and
determining a sleep stage for the individual by operating on the set of signal features using a sleep stage classifier included in a learning library, wherein the sleep stage classifier comprises a set of functions defining a likelihood that the individual is in the sleep stage based on the set of signal features.

11. The system of claim 10, wherein sampling the set of beat intervals comprises sampling using the frequency of the equally-timed segments.

12. The system of claim 10, wherein sampling the set of beat intervals comprises resampling using a frequency different from the frequency of the equally-time segments.

13. The system of claim 10, wherein the set of functions includes signal weights, and wherein each signal weight is based on a correlation between a feature in the set of signal features and a known sleep stage.

14. The system of claim 13, wherein the operations further comprise:
sampling the accelerometer signal at a first sampling rate;
differentiating the sampled accelerometer signal over each channel associated with the accelerometer signal; and
averaging a magnitude of the differentiated accelerometer signals over an accelerometer time window to generate a time-averaged motion signal;
wherein the set of signal features further comprises the time-averaged motion signal such that the sleep stage is further based on the time-averaged motion signal.

15. The system of claim 13, wherein the set of signal features further comprise an average pulse rate derived from the PPG signal sampled at a second sampling rate and a sum of the absolute energy in each of a plurality of frequency bands in the spectrogram of the interval signal.

16. The system of claim 15, wherein the sleep stage is determined from among a set of potential sleep stages, wherein the set of potential sleep stages comprises an awake stage, a non-REM stage, and a REM stage, and wherein the operations further comprise determining a sleep stage likelihood for each of the potential sleep stages based on the set of signal features and the set of signal weights in the sleep stage classifier.

17. The system of claim 16, wherein determining the sleep stage further comprises:
identifying a most likely sleep stage based on a highest sleep stage likelihood among a set of sleep stage likelihoods including each sleep stage likelihood associated with a potential sleep stage; and
determining whether the highest sleep stage likelihood exceeds a preset stage likelihood threshold.

18. The system of claim 16, wherein the learning library comprises data from among a plurality of sessions for a plurality of individuals, and wherein the set of signal weights is based on normalizing each feature in the set of features over each session for each of the plurality of individuals.

19. A tangible, non-transitory computer-readable medium storing instructions, that, when executed by at least one processor, cause the at least one processor to perform a method for probabilistically determining an individual's sleep stage, the method comprising:
receiving a set of signals from a set of sensors worn by the individual, the set of signals including a photoplethysmographic (PPG) signal and an accelerometer signal;
dividing the PPG signal into a set of equally-timed segments if the received PPG signal comprises segments having unequal time durations;
determining a beat interval associated with each segment, the beat interval reflecting an elapsed time between successive heartbeats;
sampling the set of beat intervals to generate an interval signal;
generating a set of signal features based on the interval signal and the accelerometer signal, the set of signal features including a spectrogram of the interval signal; and
determining a sleep stage for the individual by operating on the set of signal features using a sleep stage classifier included in a learning library, wherein the sleep stage classifier comprises a set of functions defining a likelihood that the individual is in the sleep stage based on the set of signal features.

20. The computer-readable medium of claim 19, wherein sampling the set of beat intervals comprises sampling using the frequency of the equally-timed segments.

21. The computer-readable medium of claim 19, wherein sampling the set of beat intervals comprises resampling using a frequency different from the frequency of the equally-time segments.

22. The computer-readable medium of claim 19, wherein the set of functions includes signal weights, each signal weight being based on a correlation between a feature in the set of signal features and a known sleep stage, wherein the learning library comprises data from among a plurality of sessions for a plurality of individuals, wherein the set of signal weights is based on normalizing each feature in the set of features over each session for each of the plurality of individuals, and wherein normalizing the spectrogram of the interval signal is based on the median of the spectrogram and not the mean.

23. The computer-readable medium of claim 22, wherein the method further comprises:
sampling the accelerometer signal at a first sampling rate;
differentiating the sampled accelerometer signal over each channel associated with the accelerometer signal; and
averaging a magnitude of the differentiated accelerometer signals over an accelerometer time window to generate a time-averaged motion signal;
wherein the set of signal features further comprises the time-averaged motion signal such that the sleep stage is further based on the time-averaged motion signal.

24. The computer-readable medium of claim 22, wherein the set of signal features further comprise an average pulse rate derived from the PPG signal sampled at a second sampling rate and a sum of the absolute energy in each of a plurality of frequency bands in the spectrogram of the interval signal.

25. The computer-readable medium of claim 24, wherein the sleep stage is determined from among a set of potential sleep stages, wherein the set of potential sleep stages comprises an awake stage, a non-REM stage, and a REM stage, and wherein the method further comprises determining a sleep stage likelihood for each of the potential sleep stages based on the set of signal features and the set of signal weights in the sleep stage classifier.

26. The computer-readable medium of claim 25, wherein determining the sleep stage further comprises:
identifying a most likely sleep stage based on a highest sleep stage likelihood among a set of sleep stage likelihoods including each sleep stage likelihood associated with a potential sleep stage; and
determining whether the highest sleep stage likelihood exceeds a preset stage likelihood threshold.

* * * * *